United States Patent
Kim et al.

(10) Patent No.: US 10,519,454 B2
(45) Date of Patent: Dec. 31, 2019

(54) **GENOME EDITING USING *CAMPYLOBACTER JEJUNI* CRISPR/CAS SYSTEM-DERIVED RGEN**

(71) Applicant: TOOLGEN INCORPORATED, Seoul (KR)

(72) Inventors: Eun Ji Kim, Seoul (KR); Seok Joong Kim, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 31 days.

(21) Appl. No.: 15/420,936

(22) Filed: Jan. 31, 2017

(65) Prior Publication Data
US 2017/0145425 A1   May 25, 2017

Related U.S. Application Data

(63) Continuation of application No. PCT/KR2015/008269, filed on Aug. 6, 2015.

(60) Provisional application No. 62/033,852, filed on Aug. 6, 2014.

(51) Int. Cl.
*C12N 15/63* (2006.01)
*C12N 9/16* (2006.01)
*C12N 7/00* (2006.01)
*C12N 15/86* (2006.01)

(52) U.S. Cl.
CPC ............. *C12N 15/63* (2013.01); *C12N 7/00* (2013.01); *C12N 9/16* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2014/0068797 A1† | 3/2014 | Doudna | |
| 2014/0186843 A1 | 7/2014 | Zhang et al. | |
| 2014/0186958 A1† | 7/2014 | Zhang | |
| 2014/0273234 A1* | 9/2014 | Zhang | C12N 15/63 435/462 |

FOREIGN PATENT DOCUMENTS

| WO | 2013/142578 A1 | 9/2013 |
| WO | 2014/065596 A1 | 5/2014 |
| WO | 2014/089290 A1 | 6/2014 |
| WO | 2014/093701 A1 | 6/2014 |
| WO | 2015/071474 A2 | 5/2015 |

OTHER PUBLICATIONS

Sampson et al entitled "A CRISPR/Cas system mediates bacterial innate immune evasion and virulence" (Nature vol. 497, pp. 254-258, published May 9, 2013). (Year: 2013).*
Fanfara et al in "Phylogeny of Cas9 determines functional exchangeability of dual-RNA and Cas9 among orthologous type II CRISPR-Cas systems" (NAR 2014 vol. 42, No. 4, pp. 2577-2590, published online Nov. 22, 2013). (Year: 2013).*
Hou, Z. et al., Efficient genome engineering in human pluripotent stem cells using Cas9 from Neisseria meningitidis:, PNAS, vol. 110, No. 39, 15644-15649.
Sapranauskas, R. et al., "The *Streptococcus thermophilus* CRISPR/Cas system provides immunity in *Escherichia coli*", Nucleic Acids Research, 2011, vol. 39, No. 21, 9275-9282.
Fonfara, Ines et al., "Phylogeny of Cas9 determines functional exchangeability of dual-RNA and Cas9 among orthologous type II CRISPR-Cas systems", Nucleic Acids Research, 2013, 1-14.
Fujii et al., "Efficient Generation of Genome-Modified Mice Using Campylobacter jejuni-Derived CRISPR/Cas", Int J Mol Sci, 18(11):1-8 (2017).
Kim et al., "In vivo genome editing with a small Cas9 orthologue derived from Campylobacter jejuni", Nat Commun, 8:1-12 (2017).
Wu et al., "Genome-wide binding of the CRISPR endonuclease Cas9 in mammalian cells", Nat Biotechnol, 32(7):670-6 (2014).
Fonfara et al., "Phylogeny of Cas9 determines functional exchangeability of dual-RNA and Cas9 among orthologous type II CRISPR-Cas systems", Nucleic Acids Res, 42(4):2577-90 (2014).
European Search Report issued in corresponding EP application No. 15830444, dated Jan. 5, 2018. 9 pp.
Ran, F. A., et al., "In vivo genome editing using *Staphylococcus aureus* Cas9", Nature (online), vol. 520, p. 186-191, Epub Apr. 1, 2015 [retrieved on Aug. 22, 2018], URL: https://www.nature.com/articles/nature14299.
Chen, B. et al., "Dynamic Imaging of Genomic Loci in Living Human Cells by an Optimized CRISPR/Cas System", Cell (online), vol. 155, p. 1479-1491.
Fujita, T. et al., "Efficient isolation of specific genomic regions and identification of associated proteins by engineered DNA-binding molecule-mediated chromatin immunoprecipitation (enChIP) using CRISPR", Biochem. Biophys. Res. Commun. (online), vol. 439, p. 132-136, Epub Aug. 11, 2013 [retrieved on Aug. 22, 2018], URL: https://www.sciencedirect.com/science/article/pii/S0006291X13013296.
Fujita et al., "Efficient isolation of specific genomic regions and identification of associated proteins by engineered DNA-binding molecule-mediated chromatin immunoprecipitation (enChIP) using CRISPR," Biochem. Biophys. Res. Commun. 439(1):132-136, (2013).†
Sapranauskas et al., "The *Streptococcus thermophilus* CRISPR/Cas system provides immunity in *Escherichia coli*," Nucleic Acids Research 39(21):9275-9282, (2011).†

* cited by examiner
† cited by third party

*Primary Examiner* — Catherine S Hibbert
(74) *Attorney, Agent, or Firm* — Mintz Levin Cohn Ferris Glovsky and Popeo, P.C.; Nicholas A. Zachariades

(57) ABSTRACT

The disclosure provided herewith relates to a *Campylobacter jejuni* CRISPR/CAS system-derived RGEN and a use thereof.

13 Claims, 14 Drawing Sheets
Specification includes a Sequence Listing.

CACATTAACCGGGCCTGGGAATATAAGGTGGTCCCAGCTCGGGGACACAGGATCCCTGGA (SEQ ID NO: 4)

Human AAVS1_C.Jejuni RGEN, 17% (2/12)

CACATTAACCGGGCCTGGGAATATAAGGTGGTCCCAGCTCGGGGACACAGGATCCCTGGA (WT, x10) (SEQ ID NO: 4)
CACATTAACCGGGCCTGGGAATATAAGGTGGTCCCAGC--GGGGACACAGGATCCCTGGA (-2, x1) (SEQ ID NO: 5)
CACATTAACCGGGCCTGGGAATATAAGGTGGTCCCAG-TCGGGGACACAGGATCCCTGGA (-1, x1) (SEQ ID NO: 6)

FIG. 3B

WT
CTTAAAGGCTAACCTGGTGTGTGGGCGGTTGTCCTGCTGCAGGGGAATTGAACAGGTGTAAAA (SEQ ID NO: 7)

Mouse Rosa26_C.Jejuni RGEN, 22% (2/9)

CTTAAAGGCTAACCTGGTGTGTGGGCGGTTGTCCTGCTGCAGGGGAATTGAACAGGTGTAAAA (WT, X7) (SEQ ID NO: 7)
CTTAAAGGCTAACCTGGTGTGTGGGGC-TTGTCCTGCAGGGGAATTGAACAGGTGTAAAA (-1, X1) (SEQ ID NO: 8)
CTTAAAGGCTAACCTGGTGTGTGGGCGGTTTGTCCTGCAGGGGAATTGAACAGGTGTAAAA (+1, X1) (SEQ ID NO: 9)

FIG. 5A sgRNA Spacer Structure (AAVS-CJ1 site as an example)
- Underbar (additional nucleotide)
- Lower case (mistmatch between sgRNA and target sequence)

| Sequence | Label |
|---|---|
| GGCCTGGAATATAAGGTGGTCCAGCTCGGGCACAC | Target sequence |
| gTATAAGGTGGTCCAGCTCGGGCACAC | GX19 |
| gATATAAGGTGGTCCAGCTCGGGCACAC | GX20 |
| GAATATAAGGTGGTCCAGCTCGGGCACAC | GX21 |
| GGAATATAAGGTGGTCCAGCTCGGGCACAC | GX22 |
| GGGAATATAAGGTGGTCCAGCTCGGGCACAC | GX23 |
| GgAATATAAGGTGGTCCAGCTCGGGCACAC | GGX20 |
| GGgAATATAAGGTGGTCCAGCTCGGGCACAC | GGGX20 |

FIG. 5B

| Target site | |
|---|---|
| hAAVS-CJ1 | GGCCCTGGGAATATAAGGTGGTCCCAGTCTGGGGACAC |
| hAAVS-NRG1 | GAGAAGGAGTAGAGGGCCACGACCTGGTGAACAC |
| hAAVS-NRG3 | CGCACCATTCTCACAAAGGAGTTTTCCACCGGACAC |
| hAAVS-NRG5 | CACCTCCTGTTAGGCAGATTCCTTATCTGGTGACACAC |

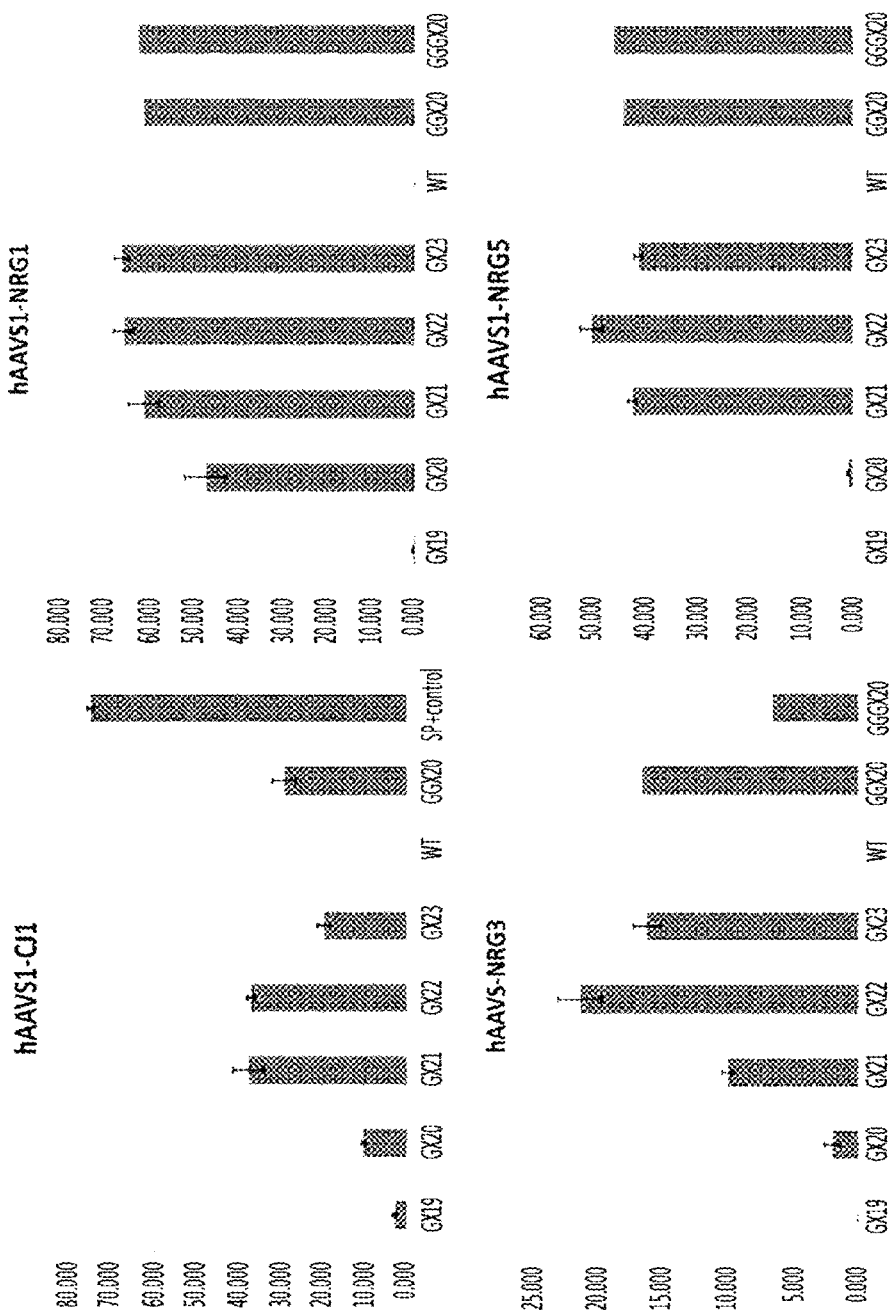

SEQUENCE LISTING

<160> NUMBER OF SEQ ID NOS: 88

<210> SEQ ID NO 1
<211> LENGTH: 8
<212> TYPE: DNA
<213> ORGANISM: Artificial Sequence
<220> FEATURE:
<223> OTHER INFORMATION: PAM sequence
<220> FEATURE:
<221> NAME/KEY: misc_feature
<222> LOCATION: (1)..(4)
<223> OTHER INFORMATION: n is a, c, g, or t

<400> SEQUENCE: 1 nnnnryac                                                          8

<210> SEQ ID NO 2
<211> LENGTH: 16
<212> TYPE: RNA
<213> ORGANISM: Artificial Sequence
<220> FEATURE:
<223> OTHER INFORMATION: stem sequence in guideRNA

<400> SEQUENCE: 2
guuuuagucc cuugug                                                 16

<210> SEQ ID NO 3

```
<211> LENGTH: 8
<212> TYPE: RNA
<213> ORGANISM: Artificial Sequence
<220> FEATURE:
<223> OTHER INFORMATION: loop sequence in guideRNA

<400> SEQUENCE: 3 auauucaa                                                                  8

<210> SEQ ID NO 4
<211> LENGTH: 60
<212> TYPE: DNA
<213> ORGANISM: Homo sapiens

<400> SEQUENCE: 4
cacattaacc ggccctggga atataaggtg gtcccagctc ggggacacag gatccctgga          60

<210> SEQ ID NO 5
<211> LENGTH: 58
<212> TYPE: DNA
<213> ORGANISM: Artificial Sequence
<220> FEATURE:
<223> OTHER INFORMATION: hAAVS1 mutant clone (-2, x1)

<400> SEQUENCE: 5
cacattaacc ggccctggga atataaggtg gtcccagcgg ggacacagga tccctgga           58

<210> SEQ ID NO 6
<211> LENGTH: 59
<212> TYPE: DNA
<213> ORGANISM: Artificial Sequence
<220> FEATURE:
<223> OTHER INFORMATION: hAAVS mutant clone (-1, x1)

<400> SEQUENCE: 6
cacattaacc ggccctggga atataaggtg gtcccagtcg gggacacagg atccctgga          59

<210> SEQ ID NO 7
<211> LENGTH: 59
<212> TYPE: DNA
<213> ORGANISM: Mus musculus

<400> SEQUENCE: 7
cttaaaggct aacctggtgt gtgggcgttg tcctgcaggg gaattgaaca ggtgtaaaa          59

<210> SEQ ID NO 8
<211> LENGTH: 58
<212> TYPE: DNA
<213> ORGANISM: Artificial Sequence
<220> FEATURE:
<223> OTHER INFORMATION: Mouse Rosa26 (-1, X1)

<400> SEQUENCE: 8
cttaaaggct aacctggtgt gtgggcttgt cctgcagggg aattgaacag gtgtaaaa          58

<210> SEQ ID NO 9
<211> LENGTH: 60
<212> TYPE: DNA
<213> ORGANISM: Artificial Sequence
<220> FEATURE:
<223> OTHER INFORMATION: Mouse Rosa26 (+1, X1)

<400> SEQUENCE: 9
cttaaaggct aacctggtgt gtgggcgttt gtcctgcagg ggaattgaac aggtgtaaaa         60
```

```
<210> SEQ ID NO 10
<211> LENGTH: 38
<212> TYPE: DNA
<213> ORGANISM: Artificial Sequence
<220> FEATURE:
<223> OTHER INFORMATION: Target sequence

<400> SEQUENCE: 10
ggccctggga atataaggtg gtcccagctc ggggacac                           38

<210> SEQ ID NO 11
<211> LENGTH: 28
<212> TYPE: DNA
<213> ORGANISM: Artificial Sequence
<220> FEATURE:
<223> OTHER INFORMATION: GX19

<400> SEQUENCE: 11
gtataaggtg gtcccagctc ggggacac                                     28

<210> SEQ ID NO 12
<211> LENGTH: 29
<212> TYPE: DNA
<213> ORGANISM: Artificial Sequence
<220> FEATURE:
<223> OTHER INFORMATION: GX20

<400> SEQUENCE: 12
gatataaggt ggtcccagct cggggacac                                    29

<210> SEQ ID NO 13
<211> LENGTH: 30
<212> TYPE: DNA
<213> ORGANISM: Artificial Sequence
<220> FEATURE:
<223> OTHER INFORMATION: GX21

<400> SEQUENCE: 13
gaatataagg tggtcccagc tcggggacac                                   30

<210> SEQ ID NO 14
<211> LENGTH: 31
<212> TYPE: DNA
<213> ORGANISM: Artificial Sequence
<220> FEATURE:
<223> OTHER INFORMATION: GX22

<400> SEQUENCE: 14
ggaatataag gtggtcccag ctcggggaca c                                 31

<210> SEQ ID NO 15
<211> LENGTH: 32
<212> TYPE: DNA
<213> ORGANISM: Artificial Sequence
<220> FEATURE:
<223> OTHER INFORMATION: GX23

<400> SEQUENCE: 15
gggaatataa ggtggtccca gctcggggac ac                                32

<210> SEQ ID NO 16
<211> LENGTH: 30
<212> TYPE: DNA
<213> ORGANISM: Artificial Sequence
<220> FEATURE:
<223> OTHER INFORMATION: GGX20
```

```
<400> SEQUENCE: 16
ggatataagg tggtcccagc tcggggacac                                           30

<210> SEQ ID NO 17
<211> LENGTH: 31
<212> TYPE: DNA
<213> ORGANISM: Artificial Sequence
<220> FEATURE:
<223> OTHER INFORMATION: GGGX20

<400> SEQUENCE: 17
gggatataag gtggtcccag ctcggggaca c                                         31

<210> SEQ ID NO 18
<211> LENGTH: 38
<212> TYPE: DNA
<213> ORGANISM: Artificial Sequence
<220> FEATURE:
<223> OTHER INFORMATION: Target site of hAAVS-CJ1

<400> SEQUENCE: 18
ggccctggga atataaggtg gtcccagctc ggggacac                                  38

<210> SEQ ID NO 19
<211> LENGTH: 38
<212> TYPE: DNA
<213> ORGANISM: Artificial Sequence
<220> FEATURE:
<223> OTHER INFORMATION: Target site of hAAVS-NRG1

<400> SEQUENCE: 19
gagaaaggga gtagaggcgg ccacgacctg gtgaacac                                  38

<210> SEQ ID NO 20
<211> LENGTH: 38
<212> TYPE: DNA
<213> ORGANISM: Artificial Sequence
<220> FEATURE:
<223> OTHER INFORMATION: Target site of hAAVS-NRG3

<400> SEQUENCE: 20
cgcaccattc tcacaaaggg agttttccac acggacac                                  38

<210> SEQ ID NO 21
<211> LENGTH: 38
<212> TYPE: DNA
<213> ORGANISM: Artificial Sequence
<220> FEATURE:
<223> OTHER INFORMATION: Target site of hAAVS-NRG5

<400> SEQUENCE: 21
cacctcctgt taggcagatt ccttatctgg tgacacac                                  38

<210> SEQ ID NO 22
<211> LENGTH: 1003
<212> TYPE: PRT
<213> ORGANISM: Campylobacter jejuni

<400> SEQUENCE: 22
```

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg

```
            35                  40                  45
Arg Leu Ala Arg Ser Ala Arg Lys Arg Leu Ala Arg Arg Lys Ala Arg
 50                  55                  60

Leu Asn His Leu Lys His Leu Ile Ala Asn Glu Phe Lys Leu Asn Tyr
 65                  70                  75                  80

Glu Asp Tyr Gln Ser Phe Asp Glu Ser Leu Ala Lys Ala Tyr Lys Gly
                 85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460
```

```
Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                    485                 490                 495

Glu Gln Asn Glu Asn Tyr Lys Ala Lys Lys Asp Ala Glu Leu Glu Cys
                500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
850                 855                 860

Ala Arg Ser Lys Lys Gly Glu Ile Lys Asp Trp Ile Leu Met Asp Glu
865                 870                 875                 880
```

```
Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
        900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
        930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys Ser Gly Pro Pro Lys Lys Lys Arg
        980                 985                 990

Lys Val Tyr Pro Tyr Asp Val Pro  Asp Tyr Ala
        995                 1000

<210> SEQ ID NO 23
<211> LENGTH: 100
<212> TYPE: DNA
<213> ORGANISM: Artificial Sequence
<220> FEATURE:
<223> OTHER INFORMATION: C.jejuni_sgRNA
<220> FEATURE:
<221> NAME/KEY: misc_feature
<222> LOCATION: (1)..(20)
<223> OTHER INFORMATION: n is a, c, g, or t

<400> SEQUENCE: 23
nnnnnnnnnn nnnnnnnnnn gttttagtcc ctgaaaaggg actaaaataa agagtttgcg    60
ggactctgcg gggttacaat cccctaaaac cgcttttttt                         100

<210> SEQ ID NO 24
<211> LENGTH: 27
<212> TYPE: DNA
<213> ORGANISM: Artificial Sequence
<220> FEATURE:
<223> OTHER INFORMATION: Target sequence of Human AAVS1

<400> SEQUENCE: 24
atataaggtg gtcccagctc ggggaca                                        27

<210> SEQ ID NO 25
<211> LENGTH: 27
<212> TYPE: DNA
<213> ORGANISM: Artificial Sequence
<220> FEATURE:
<223> OTHER INFORMATION: Target sequence of Mouse Rosa26

<400> SEQUENCE: 25
attcccctgc aggacaacgc ccacaca                                        27

<210> SEQ ID NO 26
<211> LENGTH: 20
<212> TYPE: DNA
<213> ORGANISM: Artificial Sequence
<220> FEATURE:
<223> OTHER INFORMATION: Human AAVS1-F

<400> SEQUENCE: 26
tgcttctcct cttgggaagt                                                20
```

```
<210> SEQ ID NO 27
<211> LENGTH: 20
<212> TYPE: DNA
<213> ORGANISM: Artificial Sequence
<220> FEATURE:
<223> OTHER INFORMATION: Human AAVS1-R

<400> SEQUENCE: 27
ccccgttctc ctgtggattc                                                    20

<210> SEQ ID NO 28
<211> LENGTH: 20
<212> TYPE: DNA
<213> ORGANISM: Artificial Sequence
<220> FEATURE:
<223> OTHER INFORMATION: Mouse Rosa26-F

<400> SEQUENCE: 28
acgtttccga cttgagttgc                                                    20

<210> SEQ ID NO 29
<211> LENGTH: 20
<212> TYPE: DNA
<213> ORGANISM: Artificial Sequence
<220> FEATURE:
<223> OTHER INFORMATION: Mouse Rosa26-R

<400> SEQUENCE: 29
cccagctaca gcctcgattt                                                    20

<210> SEQ ID NO 30
<211> LENGTH: 108
<212> TYPE: DNA
<213> ORGANISM: Artificial Sequence
<220> FEATURE:
<223> OTHER INFORMATION: C.jejuni_sgRNA_stem modified
<220> FEATURE:
<221> NAME/KEY: misc_feature
<222> LOCATION: (1)..(20)
<223> OTHER INFORMATION: n is a, c, g, or t

<400> SEQUENCE: 30
nnnnnnnnnn nnnnnnnnnn gttttagtcc cttgtggaaa tataagggac taaaataaag        60
agtttgcggg actctgcggg gttacaatcc cctaaaaccg ctttttttt                   108

<210> SEQ ID NO 31
<211> LENGTH: 104
<212> TYPE: DNA
<213> ORGANISM: Artificial Sequence
<220> FEATURE:
<223> OTHER INFORMATION: C.jejuni_sgRNA_loop modified
<220> FEATURE:
<221> NAME/KEY: misc_feature
<222> LOCATION: (1)..(20)
<223> OTHER INFORMATION: n is a, c, g, or t

<400> SEQUENCE: 31
nnnnnnnnnn nnnnnnnnnn gttttagtcc ctatattcaa agggactaaa ataaagagtt        60
tgcgggactc tgcggggtta caatccccta aaaccgcttt tttt                        104

<210> SEQ ID NO 32
<211> LENGTH: 27
<212> TYPE: DNA
<213> ORGANISM: Artificial Sequence
<220> FEATURE:
<223> OTHER INFORMATION: Human AAVS1-CJ1
```

```
<400> SEQUENCE: 32
atataaggtg gtcccagctc ggggaca                                           27

<210> SEQ ID NO 33
<211> LENGTH: 27
<212> TYPE: DNA
<213> ORGANISM: Artificial Sequence
<220> FEATURE:
<223> OTHER INFORMATION: Human AAVS1-NRG1

<400> SEQUENCE: 33
gtagaggcgg ccacgacctg gtgaaca                                           27

<210> SEQ ID NO 34
<211> LENGTH: 27
<212> TYPE: DNA
<213> ORGANISM: Artificial Sequence
<220> FEATURE:
<223> OTHER INFORMATION: Human AAVS1-NRG3

<400> SEQUENCE: 34
tcacaaaggg agttttccac acggaca                                           27

<210> SEQ ID NO 35
<211> LENGTH: 27
<212> TYPE: DNA
<213> ORGANISM: Artificial Sequence
<220> FEATURE:
<223> OTHER INFORMATION: Human AAVS1-NRG5

<400> SEQUENCE: 35
taggcagatt ccttatctgg tgacaca                                           27

<210> SEQ ID NO 36
<211> LENGTH: 53
<212> TYPE: DNA
<213> ORGANISM: Artificial Sequence
<220> FEATURE:
<223> OTHER INFORMATION: AS-AV-F1

<400> SEQUENCE: 36
acactctttc cctacacgac gctcttccga tctaggagga ggcctaagga tgg              53

<210> SEQ ID NO 37
<211> LENGTH: 53
<212> TYPE: DNA
<213> ORGANISM: Artificial Sequence
<220> FEATURE:
<223> OTHER INFORMATION: AS-AV-F2

<400> SEQUENCE: 37
acactctttc cctacacgac gctcttccga tctgctctgg gcggaggaat atg              53

<210> SEQ ID NO 38
<211> LENGTH: 53
<212> TYPE: DNA
<213> ORGANISM: Artificial Sequence
<220> FEATURE:
<223> OTHER INFORMATION: AS-AV-F4

<400> SEQUENCE: 38
acactctttc cctacacgac gctcttccga tctatcctct ctggctccat cgt              53

<210> SEQ ID NO 39
<211> LENGTH: 54
```

<212> TYPE: DNA
<213> ORGANISM: Artificial Sequence
<220> FEATURE:
<223> OTHER INFORMATION: AS-AV-R1

<400> SEQUENCE: 39
gtgactggag ttcagacgtg tgctcttccg atcttgtcat ggcatcttcc aggg        54

<210> SEQ ID NO 40
<211> LENGTH: 54
<212> TYPE: DNA
<213> ORGANISM: Artificial Sequence
<220> FEATURE:
<223> OTHER INFORMATION: AS-AV-R2

<400> SEQUENCE: 40
gtgactggag ttcagacgtg tgctcttccg atcttccgtg cgtcagtttt acct        54

<210> SEQ ID NO 41
<211> LENGTH: 54
<212> TYPE: DNA
<213> ORGANISM: Artificial Sequence
<220> FEATURE:
<223> OTHER INFORMATION: AS-AV-R4

<400> SEQUENCE: 41
gtgactggag ttcagacgtg tgctcttccg atctccggtt aatgtggctc tggt        54

<210> SEQ ID NO 42
<211> LENGTH: 28
<212> TYPE: DNA
<213> ORGANISM: Artificial Sequence
<220> FEATURE:
<223> OTHER INFORMATION: Test sequence

<400> SEQUENCE: 42
atataaggtg gtcccagctc ggggacac                                     28

<210> SEQ ID NO 43
<211> LENGTH: 28
<212> TYPE: DNA
<213> ORGANISM: Artificial Sequence
<220> FEATURE:
<223> OTHER INFORMATION: Test sequence

<400> SEQUENCE: 43 tggcccact gtggggtgga ggggacag                                      28

<210> SEQ ID NO 44
<211> LENGTH: 28
<212> TYPE: DNA
<213> ORGANISM: Artificial Sequence
<220> FEATURE:
<223> OTHER INFORMATION: Test sequence

<400> SEQUENCE: 44
caccccacag tggggccact agggacag                                     28

<210> SEQ ID NO 45
<211> LENGTH: 28
<212> TYPE: DNA
<213> ORGANISM: Artificial Sequence
<220> FEATURE:
<223> OTHER INFORMATION: Test sequence

<400> SEQUENCE: 45

```
ctagcagcaa accttccctt cactacaa                                          28

<210> SEQ ID NO 46
<211> LENGTH: 28
<212> TYPE: DNA
<213> ORGANISM: Artificial Sequence
<220> FEATURE:
<223> OTHER INFORMATION: Test sequence

<400> SEQUENCE: 46
ctccatgaat gcaaactgtt ttatacat                                          28

<210> SEQ ID NO 47
<211> LENGTH: 28
<212> TYPE: DNA
<213> ORGANISM: Artificial Sequence
<220> FEATURE:
<223> OTHER INFORMATION: Test sequence

<400> SEQUENCE: 47
tgcattcatg gagggcaact aaatacat                                          28

<210> SEQ ID NO 48
<211> LENGTH: 28
<212> TYPE: DNA
<213> ORGANISM: Artificial Sequence
<220> FEATURE:
<223> OTHER INFORMATION: Test sequence

<400> SEQUENCE: 48
atcaagtgtc aagtccaatc tatgacat                                          28

<210> SEQ ID NO 49
<211> LENGTH: 28
<212> TYPE: DNA
<213> ORGANISM: Artificial Sequence
<220> FEATURE:
<223> OTHER INFORMATION: Test sequence

<400> SEQUENCE: 49
ccaatctatg acatcaatta ttatacat                                          28

<210> SEQ ID NO 50
<211> LENGTH: 28
<212> TYPE: DNA
<213> ORGANISM: Artificial Sequence
<220> FEATURE:
<223> OTHER INFORMATION: Test sequence

<400> SEQUENCE: 50
gcaaaaggct gaagagcatg actgacat                                          28

<210> SEQ ID NO 51
<211> LENGTH: 28
<212> TYPE: DNA
<213> ORGANISM: Artificial Sequence
<220> FEATURE:
<223> OTHER INFORMATION: Test sequence

<400> SEQUENCE: 51
gcagcatagt gagcccagaa ggggacag                                          28

<210> SEQ ID NO 52
<211> LENGTH: 28
<212> TYPE: DNA
<213> ORGANISM: Artificial Sequence
```

<220> FEATURE:
<223> OTHER INFORMATION: Test sequence

<400> SEQUENCE: 52
gccgcccagt gggactttgg aaatacaa                                          28

<210> SEQ ID NO 53
<211> LENGTH: 28
<212> TYPE: DNA
<213> ORGANISM: Artificial Sequence
<220> FEATURE:
<223> OTHER INFORMATION: Test sequence

<400> SEQUENCE: 53
tccactgcag ctcccttact gataacaa                                          28

<210> SEQ ID NO 54
<211> LENGTH: 28
<212> TYPE: DNA
<213> ORGANISM: Artificial Sequence
<220> FEATURE:
<223> OTHER INFORMATION: Test sequence

<400> SEQUENCE: 54
attcccctgc aggacaacgc ccacacac                                          28

<210> SEQ ID NO 55
<211> LENGTH: 28
<212> TYPE: DNA
<213> ORGANISM: Artificial Sequence
<220> FEATURE:
<223> OTHER INFORMATION: Test sequence

<400> SEQUENCE: 55
acacctgttc aattccsctg caggacaa                                          28

<210> SEQ ID NO 56
<211> LENGTH: 28
<212> TYPE: DNA
<213> ORGANISM: Artificial Sequence
<220> FEATURE:
<223> OTHER INFORMATION: Test sequence

<400> SEQUENCE: 56
ttgaacaggt gtaaaattgg agggacaa                                          28

<210> SEQ ID NO 57
<211> LENGTH: 28
<212> TYPE: DNA
<213> ORGANISM: Artificial Sequence
<220> FEATURE:
<223> OTHER INFORMATION: Test sequence

<400> SEQUENCE: 57
ttgcccctat taaaaaactt cccgacaa                                          28

<210> SEQ ID NO 58
<211> LENGTH: 28
<212> TYPE: DNA
<213> ORGANISM: Artificial Sequence
<220> FEATURE:
<223> OTHER INFORMATION: Test sequence

<400> SEQUENCE: 58
agatccttac tacagtatga aattacag                                          28

<210> SEQ ID NO 59
<211> LENGTH: 28
<212> TYPE: DNA
<213> ORGANISM: Artificial Sequence
<220> FEATURE:
<223> OTHER INFORMATION: Test sequence

<400> SEQUENCE: 59
agccttatca aaaggtattt tagaacac                                        28

<210> SEQ ID NO 60
<211> LENGTH: 28
<212> TYPE: DNA
<213> ORGANISM: Artificial Sequence
<220> FEATURE:
<223> OTHER INFORMATION: Test sequence

<400> SEQUENCE: 60
cggggcccac tcaccgtgca cataacag                                        28

<210> SEQ ID NO 61
<211> LENGTH: 28
<212> TYPE: DNA
<213> ORGANISM: Artificial Sequence
<220> FEATURE:
<223> OTHER INFORMATION: Test sequence

<400> SEQUENCE: 61
gccgtgtccg cgccatggcc atctacaa                                        28

<210> SEQ ID NO 62
<211> LENGTH: 28
<212> TYPE: DNA
<213> ORGANISM: Artificial Sequence
<220> FEATURE:
<223> OTHER INFORMATION: Test sequence

<400> SEQUENCE: 62
tggccatcta caagaagtca cagcacat                                        28

<210> SEQ ID NO 63
<211> LENGTH: 28
<212> TYPE: DNA
<213> ORGANISM: Artificial Sequence
<220> FEATURE:
<223> OTHER INFORMATION: Test sequence

<400> SEQUENCE: 63
ccgagtgtca ggagctcctg cagcacag                                        28

<210> SEQ ID NO 64
<211> LENGTH: 28
<212> TYPE: DNA
<213> ORGANISM: Artificial Sequence
<220> FEATURE:
<223> OTHER INFORMATION: Test sequence

<400> SEQUENCE: 64
ctccccgggg cccactcacc gtgcacat                                        28

<210> SEQ ID NO 65
<211> LENGTH: 28
<212> TYPE: DNA
<213> ORGANISM: Artificial Sequence
<220> FEATURE:
<223> OTHER INFORMATION: Test sequence

```
<400> SEQUENCE: 65
cctgtgcagt tgtgggtcag cgccacac                                              28

<210> SEQ ID NO 66
<211> LENGTH: 28
<212> TYPE: DNA
<213> ORGANISM: Artificial Sequence
<220> FEATURE:
<223> OTHER INFORMATION: Test sequence

<400> SEQUENCE: 66
ggtgtggcgc tgacccacaa ctgcacag                                              28

<210> SEQ ID NO 67
<211> LENGTH: 28
<212> TYPE: DNA
<213> ORGANISM: Artificial Sequence
<220> FEATURE:
<223> OTHER INFORMATION: Test sequence

<400> SEQUENCE: 67
ttcttgtaga tggccatggc gcggacac                                              28

<210> SEQ ID NO 68
<211> LENGTH: 28
<212> TYPE: DNA
<213> ORGANISM: Artificial Sequence
<220> FEATURE:
<223> OTHER INFORMATION: Test sequence

<400> SEQUENCE: 68
cgccatggcc atctacaaga agtcacag                                              28

<210> SEQ ID NO 69
<211> LENGTH: 28
<212> TYPE: DNA
<213> ORGANISM: Artificial Sequence
<220> FEATURE:
<223> OTHER INFORMATION: Test sequence

<400> SEQUENCE: 69
acatcatcaa tattgttcct gtatacac                                              28

<210> SEQ ID NO 70
<211> LENGTH: 28
<212> TYPE: DNA
<213> ORGANISM: Artificial Sequence
<220> FEATURE:
<223> OTHER INFORMATION: Test sequence

<400> SEQUENCE: 70
tgaatccaaa aaccttaaaa caaaacaa                                              28

<210> SEQ ID NO 71
<211> LENGTH: 28
<212> TYPE: DNA
<213> ORGANISM: Artificial Sequence
<220> FEATURE:
<223> OTHER INFORMATION: Test sequence

<400> SEQUENCE: 71
tgctttgaat ccaaaaacct taaaacaa                                              28

<210> SEQ ID NO 72
```

```
<210> SEQ ID NO 72
<211> LENGTH: 28
<212> TYPE: DNA
<213> ORGANISM: Artificial Sequence
<220> FEATURE:
<223> OTHER INFORMATION: Test sequence

<400> SEQUENCE: 72
agcataaaaa ccattacaag atatacaa                                              28

<210> SEQ ID NO 73
<211> LENGTH: 28
<212> TYPE: DNA
<213> ORGANISM: Artificial Sequence
<220> FEATURE:
<223> OTHER INFORMATION: Test sequence

<400> SEQUENCE: 73
gtagatgtgc tgagagacat tatgacac                                              28

<210> SEQ ID NO 74
<211> LENGTH: 28
<212> TYPE: DNA
<213> ORGANISM: Artificial Sequence
<220> FEATURE:
<223> OTHER INFORMATION: Test sequence

<400> SEQUENCE: 74
ggcggtgtca taatgtctct cagcacat                                              28

<210> SEQ ID NO 75
<211> LENGTH: 28
<212> TYPE: DNA
<213> ORGANISM: Artificial Sequence
<220> FEATURE:
<223> OTHER INFORMATION: Test sequence

<400> SEQUENCE: 75
atttaactgc agaggtatgt ataaacat                                              28

<210> SEQ ID NO 76
<211> LENGTH: 30
<212> TYPE: DNA
<213> ORGANISM: Artificial Sequence
<220> FEATURE:
<223> OTHER INFORMATION: Target sequence

<400> SEQUENCE: 76
gccacgacct ggtgaacacc taggacgcac                                            30

<210> SEQ ID NO 77
<211> LENGTH: 30
<212> TYPE: DNA
<213> ORGANISM: Artificial Sequence
<220> FEATURE:
<223> OTHER INFORMATION: Target sequence

<400> SEQUENCE: 77
ggccttatct cacaggtaaa actgacgcac                                            30

<210> SEQ ID NO 78
<211> LENGTH: 30
<212> TYPE: DNA
<213> ORGANISM: Artificial Sequence
<220> FEATURE:
<223> OTHER INFORMATION: Target sequence

<400> SEQUENCE: 78
```
ctcttgggaa gtgtaaggaa gctgcagcac                                            30

<210> SEQ ID NO 79
<211> LENGTH: 30
<212> TYPE: DNA
<213> ORGANISM: Artificial Sequence
<220> FEATURE:
<223> OTHER INFORMATION: Target sequence

<400> SEQUENCE: 79
agctgcagca ccaggatcag tgaaacgcac                                            30

<210> SEQ ID NO 80
<211> LENGTH: 30
<212> TYPE: DNA
<213> ORGANISM: Artificial Sequence
<220> FEATURE:
<223> OTHER INFORMATION: Target sequence

<400> SEQUENCE: 80
ctgtggggtg gaggggacag ataaaagtac                                            30

<210> SEQ ID NO 81
<211> LENGTH: 30
<212> TYPE: DNA
<213> ORGANISM: Artificial Sequence
<220> FEATURE:
<223> OTHER INFORMATION: Target sequence

<400> SEQUENCE: 81
gccggttaat gtggctctgg ttctgggtac                                            30

<210> SEQ ID NO 82
<211> LENGTH: 30
<212> TYPE: DNA
<213> ORGANISM: Artificial Sequence
<220> FEATURE:
<223> OTHER INFORMATION: Target sequence

<400> SEQUENCE: 82
gccatgacag ggggctggaa gagctagcac                                            30

<210> SEQ ID NO 83
<211> LENGTH: 20
<212> TYPE: DNA
<213> ORGANISM: Artificial Sequence
<220> FEATURE:
<223> OTHER INFORMATION: Target sequence

<400> SEQUENCE: 83
gagaaccaga ccacccagaa                                                       20

<210> SEQ ID NO 84
<211> LENGTH: 20
<212> TYPE: DNA
<213> ORGANISM: Artificial Sequence
<220> FEATURE:
<223> OTHER INFORMATION: Target sequence

<400> SEQUENCE: 84
ggcagccccg ccatcaagaa                                                       20

<210> SEQ ID NO 85
<211> LENGTH: 20
<212> TYPE: DNA

```
<213> ORGANISM: Artificial Sequence
<220> FEATURE:
<223> OTHER INFORMATION: Target sequence

<400> SEQUENCE: 85
gtaagatgct tttctgtgac                                              20

<210> SEQ ID NO 86
<211> LENGTH: 20
<212> TYPE: DNA
<213> ORGANISM: Artificial Sequence
<220> FEATURE:
<223> OTHER INFORMATION: Target sequence

<400> SEQUENCE: 86
gatcctttga tcttttctac                                              20

<210> SEQ ID NO 87
<211> LENGTH: 20
<212> TYPE: DNA
<213> ORGANISM: Artificial Sequence
<220> FEATURE:
<223> OTHER INFORMATION: Target sequence

<400> SEQUENCE: 87
gcctccaaaa aagaagagaa                                              20

<210> SEQ ID NO 88
<211> LENGTH: 20
<212> TYPE: DNA
<213> ORGANISM: Artificial Sequence
<220> FEATURE:
<223> OTHER INFORMATION: Target sequence

<400> SEQUENCE: 88
tgacatcaat tattatacat                                              20
```

GENOME EDITING USING *CAMPYLOBACTER JEJUNI* CRISPR/CAS SYSTEM-DERIVED RGEN

CROSS-REFERENCE TO RELATED APPLICATION(S)

This application is a Continuation application of International Application No. PCT/KR2015/008269, filed Aug. 6, 2015, designating the United States of America, which claims the benefit of U.S. Provisional Application No. 62/033,852, filed Aug. 6, 2014, which applications are incorporated herein by reference in their entirety.

REFERENCE TO SEQUENCE LISTING

The contents of the text file named "52029-501C01US_ST25.txt" which was created on Jan. 31, 2017, and is 25641 bytes, are hereby incorporated by reference in their entireties.

TECHNICAL FIELD

The disclosure provided herewith relates to a *Campylobacter jejuni* CRISPR/CAS system-derived, RNA-guided engineered nuclease (RGEN) and methods for using the same.

BACKGROUND ART

Engineered nucleases can be used to effectively manipulate genes in living cells or whole organisms by creating site-specific double-strand breaks at desired locations in the genome (Nat Rev Genet, 2014. 15(5): p. 321-34.). Engineered nucleases, which comprise a DNA-binding domain and a nuclease domain customized for type II restriction enzymes, have a broad spectrum of genome engineering applications in the biotechnology and medical fields as well as various other industries. More recently, a more potent RGEN platform has been developed based on the CRISPR/CAS9 bacterial adaptive immune system.

The sequence that RGEN targets is limited to a protospacer adjacent motif (PAM), which is a DNA sequence immediately following the DNA sequence targeted by the Cas9 nuclease. The PAM sequence was not previously reprogrammable in the CRISPR bacterial adaptive immune system. The canonical PAM comprises the sequence 5'-NGG-3' and is associated with the RGEN derived from the CAS9 nuclease of *Streptococcus pyogenes*. Hence, the GG motif is a prerequisite for DNA recognition by the RGEN. To expand sequences for use as PAMs, attempts have been made to separate RGENs from different bacterial species with versatile PAMs. In fact, different PAMs have been found to be associated with the CAS9 protein of the bacteria *Streptococcus thermophilus* (PAM: NNAGAAW) and *Neisseria meningitidis* (PAM: NNNNGATT), widening the range of selection in determining RGEN target loci.

SUMMARY

As described herein, intensive and thorough research into the development of RGENs from bacteria other than *Streptococcus pyogenes* has resulted in the discovery that a Cas protein derived from *Campylobacter jejuni* (*C. jejuni*) specifically recognizes an NNNNRYAC sequence, which can be used as a PAM in the targeting of a DNA of interest. Further, a guide RNA can be engineered for optimal of a DNA, thereby resulting in efficient genome editing, transcription regulation, and separation of a DNA of interest.

Accordingly, in one aspect, the present invention provides a method for targeting a DNA sequence comprising a PAM sequence of SEQ ID NO: 1, the method comprising introducing a Cas protein that recognizes the PAM sequence of SEQ ID NO: 1, or a nucleic acid encoding the Cas protein into a cell.

In another aspect, the present invention provides an isolated guide RNA comprising a sequence capable of forming a duplex (forming a base pair or hybridizing) with a complementary strand of a target DNA sequence of interest adjacent to the PAM sequence of SEQ ID NO: 1, or a composition comprising the same.

In still another aspect, the disclosure provided herewith provides a CRISPR-CAS system, comprising: (i) a guide RNA comprising a sequence capable of duplexing with a target NDA sequence adjacent to the PAM sequence of NNNNRYAC (SEQ ID NO: 1), or DNA encoding the guide RNA, and (ii) a Cas protein recognizing the NNNNRYAC sequence (SEQ ID NO: 1), or a nucleic acid encoding the Cas protein.

In still another aspect, the disclosure provided herewith provides a recombinant viral vector, comprising (i) an expression cassette for a guide RNA comprising a sequence capable of forming a duplex with a target DNA sequence adjacent to the PAM sequence NNNNRYAC (SEQ ID NO: 1), and (ii) an expression cassette for a Cas protein recognizing the PAM sequence NNNNRYAC (SEQ ID NO: 1).

In still another aspect, the disclosure provides an isolated guide RNA comprising a sequence, 21-23 bp in length, capable of forming a duplex with a complementary strand of a target DNA sequence, or a composition comprising the same.

In still another aspect, the disclosure provides an isolated guide RNA, comprising: a first region comprising a sequence capable of forming a duplex with a complementary strand of a target DNA sequence, and a second region comprising a stem-loop structure characterized by a stem 13-18 bp in length, or a composition comprising the isolated guide RNA.

In still another aspect, the disclosure provides an isolated guide RNA, comprising: a first region comprising a sequence capable of forming a duplex with a complementary strand of a target DNA sequence, and a second region comprising a stem-loop structure characterized by a loop 5-10 bp in length, or a composition comprising the isolated guide RNA.

In still another aspect, the disclosure provided herewith provides a method of genome editing in a cell, comprising introducing an isolated guide RNA or a DNA encoding the isolated guide RNA, along with a Cas protein or a nucleic acid encoding the Cas protein, into the cell.

In still another aspect, the disclosure provides a method of cleaving a target DNA in a cell, comprising introducing an isolated guide RNA or a DNA encoding the isolated guide RNA, and a Cas protein or a nucleic acid encoding the Cas protein into the cell.

In still another aspect, the disclosure provides a method for preparing a target DNA-recognizing sequence of a guide RNA, comprising: (i) identifying the presence of a PAM sequence NNNNRYAC (SEQ ID NO: 1) in a given sequence; and (ii) determining a sequence located upstream of the PAM sequence NNNNRYAC (SEQ ID NO: 1) as being recognizable by a guide RNA, if the presence of the PAM sequence is identified in step (i).

In still another aspect, the disclosure provides a method for isolating a DNA of interest, comprising: (i) introducing a guide RNA or a DNA encoding the guide RNA, along with a deactivated Cas protein or a nucleic acid encoding the deactivated Cas protein, into a cell, to allow the guide RNA and the deactivated Cas protein to form a complex together with the DNA of interest comprising a target DNA sequence; and (ii) separating the complex from a sample.

In still another aspect, the disclosure provides a method for Cas-mediated gene expression regulation in a DNA of interest comprising a target DNA sequence, comprising introducing an isolated guide RNA specifically recognizing the target DNA sequence or a DNA encoding the guide RNA, and an deactivated Cas protein fused to a transcription effector domain or a nucleic acid encoding the deactivated Cas protein into a cell.

As described above, in some embodiments, the CRISPR/Cas system can be effectively used for targeting a target DNA, thereby achieving genome editing, transcription regulation, and isolation of a DNA of interest.

BRIEF DESCRIPTION OF DRAWINGS

FIG. 2A and FIG. 2B depict the experiments for *C. jejuni* RGEN-induced mutation in an endogenous human AAVS1 target locus. FIG. 2A shows that RGEN-driven chromosomal mutations were detected using a T7E1 assay. Asterisks (*) indicate DNA bands that are anticipated to be cleaved by T7E1. HEK293 wild-type (wt) gDNA was used as a negative control (−). A previously proven RGEN was used as a positive control (+). FIG. 2B shows DNA sequences of hAAVS1 mutant clones. Target sequence regions complementary to chimeric RNA are shown in bold. PAM sequences recognized by CAS9 are underlined. The WT sequence of FIG. 2B is represented by SEQ ID NO: 4, the (−2, x1) sequence by SEQ ID NO: 5, and the (−1, x1) sequence by SEQ ID NO: 6.

FIG. 3A and FIG. 3B show the experiments for *C. jejuni* RGEN-induced mutation in an endogenous mouse ROSA26 (mROSA) target locus. FIG. 3A shows that RGEN-driven chromosomal mutations were detected using a T7E1 assay. Asterisks (*) indicate DNA bands that are anticipated to be cleaved by T7E1. NIH3T3 wt gDNA was used as a negative control (−). A previously proven RGEN was used as a positive control (+). FIG. 3B shows DNA sequences of mROSA mutant clones. Target sequence regions complementary to chimeric RNA are shown in bold. PAM sequences recognized by *C. jejuni* CAS9 are underlined. The WT sequence of FIG. 3B is represented by SEQ ID NO: 7, the (−1, x1) sequence by SEQ ID NO: 8, and the (+1, x1) sequence by SEQ ID NO: 9.

FIG. 5A to FIG. 5C illustrate the optimization of the spacer length of sgRNAs. FIG. 5A shows various sgRNA structures. Additional nucleotides immediately upstream of the 5' end of the spacer of sgRNA are underlined, wherein small letters represent mismatched nucleotides with regard to the target sequence. The PAM sequence is boxed. In FIG. 5A, the target sequence is represented by SEQ ID NO: 10, GX19 by SEQ ID NO: 11, GX20 by SEQ ID NO: 12, GX21 by SEQ ID NO: 13, GX22 by SEQ ID NO: 14, GX23 by SEQ ID NO: 15, GGX20 by SEQ ID NO: 16, and GGGX20 by SEQ ID NO: 17. FIG. 5B shows target sites of sgRNA wherein sequences for hAAVS-CJ1, hAAVS-NRG1, hAAVS-NRG3, and hAAVS-NRG5 are represented by SEQ ID NOs: 18, 19, 20, and 21, respectively. FIG. 5C shows the efficiency of the sgRNA constructs in inducing RGEN-mediated mutations. Briefly, sgRNAs were constructed to have various lengths of spacers (19-23 bp) and various numbers of additional G (guanine) residues present immediately upstream of the spacer. Each of the sgRNAs shown in FIG. 5A was designed for 4 target sites of the human AAVS1 locus (FIG. 5B), and was delivered to human 293-cells. Subsequently, mutations induced by NHEJ were identified in the cells. In this embodiment, the target sites were amplified by PCR, and analyzed by deep sequencing using miSEQ (Illumine) to detect the mutations. On the whole, genome editing (mutation) frequency was increased when the recognition sequence was 21-23 bp in length or was provided with 2 or 3 additional G residues at the 5' end thereof, compared to GX19 or GX20 used in *C. jejuni* or other species.

DETAILED DESCRIPTION OF CERTAIN EMBODIMENTS

Figure 1:
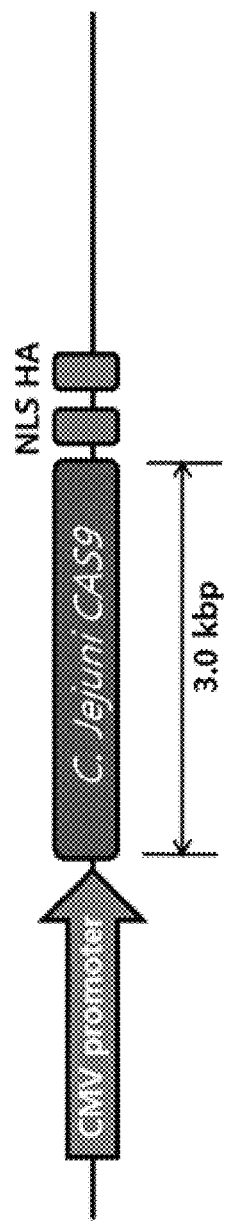
FIG. 1 depicts a schematic diagram of a *C. jejuni* Cas9 expression vector. The vector is designed so that a humanized Cas9 protein is expressed under the regulation of a CMV promoter and is provided with a nuclear localization signal (NLS) and an HA tag at a C-terminal region.

One embodiment of the present invention provides a method for targeting a DNA sequence of interest, comprising introducing into a cell a Cas protein or a nucleic acid encoding the same.

In detail, in accordance with one aspect, the present disclosure provides a method for targeting a DNA sequence comprising a PAM (protospacer adjacent motif) sequence of SEQ ID NO: 1, comprising introducing a Cas protein that recognizes the PAM sequence NNNNRYAC of SEQ ID NO: 1 or a nucleic acid encoding the Cas protein into a cell. In SEQ ID NO: 1, according to the IUPAC nomenclature, "N" refers to any nucleotide, for example, selected from A, C, G, and T; "R" refers to purine (A/G); and "Y" refers to pyrimidine (C/T).

In an aspect of the present disclosure, the method may further comprise introducing a guide RNA comprising a sequence capable of forming a duplex with a complementary strand of a DNA of interest (target DNA) adjacent to the PAM sequence of SEQ ID NO: 1. The guide RNA can be introduced simultaneously or sequentially with the Cas protein that recognizes the PAM sequence of SEQ ID NO: 1 or the nucleic acid encoding the Cas protein. As used herein, the term "targeting" is intended to encompass the binding of a Cas protein to a DNA sequence of interest, either with or without DNA cleavage. The terminology that will be described later is applicable to all embodiments of the present disclosure, and can be used in combination.

The Cas protein can perform its activity after forming a complex with CRISPR RNA (crRNA) and trans-activating crRNA (tracrRNA). The Cas protein may exhibit endonuclease or nickase activity.

Information related to Cas proteins or genes encoding Cas proteins can be found in well-known databases, such as GenBank of the NCBI (National Center for Biotechnology Information). According to one embodiment, the Cas protein may be a Cas9 protein. In another embodiment, the Cas protein may be one originating (derived) from a *Campylobacter* spp. (i.e., the genus *Campylobacter*) and may particularly be of *Campylobacter jejuni* in origin. More particularly, the Cas9 protein can be derived from *Campylobacter jejuni*. In some embodiments of the present disclosure, the Cas protein may comprise the amino acid sequence represented by SEQ ID NO: 22, or may be homologous to the amino acid sequence of SEQ ID NO: 22, retaining the intrinsic activity thereof. For example, without limitation, the Cas protein and its homologous sequences encompassed by the present disclosure may have a sequence identity at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 22.

Moreover, the Cas protein, as used in certain embodiments of the present disclosure, is intended to encompass any variant that can serve as an activated endonuclease or nickase in cooperation with a guide RNA, as well as a native protein. The activated endonuclease or nickase may cleave a target DNA, or may be able to perform genome editing with the cleavage function. As for deactivated variants, their functions may be used for regulating transcription or isolating a DNA of interest.

The Cas9 protein variant may be a derivative, variant, or mutant of Cas9 resulting from the substitution of a catalytic aspartate or histidine residue with a different amino acid. For example, the different amino acid may be alanine, but is not limited thereto.

Specifically, the Cas protein, for example, a Cas9 protein derived from *C. jejuni* may include a substitution of the catalytic aspartic acid (D) at position 8 or the histidine residue (H) at position 559 with an amino acid that differs from the wild type amino acid sequence. In some embodiments, the catalytic aspartic acid (D) at position 8 or the histidine residue (H) at position 559 of the sequence of SEQ ID NO. 22 is substituted with a different amino acid. For example, the different amino acid may be, without limitation, alanine. The Cas9 nuclease variant prepared by introducing a mutation to one active site of the native Cas9 nuclease can act as a nickase in association with a guide RNA. When bound to one guide RNA molecule, two nickase molecules can cleave both strands of a DNA duplex of interest, thereby creating double-strand breaks (DSB). Hence, such variants also belong to the scope of RGENs encompassed by the present disclosure.

As used herein, the term "deactivated Cas protein" refers to a Cas nuclease, the function of which is entirely or partially deactivated. The deactivated Cas protein may be abbreviated to dCas. The Cas may be a Cas9 protein. Further, it may originate from *Campylobacter* spp., and particularly from *C. jejuni*. Any method may be used in the preparation of the deactivated Cas9 nuclease, so long as it eliminates nuclease activity. For example, a dCAS9 protein can be constructed by introducing mutations into the two above-mentioned active loci of the Cas9 nuclease. The dCAS9 can then act as a DNA-bound complex with a guide DNA, while lacking a DNA cleavage function. Moreover, the dCAS9 protein may have substituents having other than the aspartic acid (D) at position 8 and the histidine (H) at position 559. For example, in some embodiments, the dCAS9 protein may have substituents other than the aspartic acid (D) at position 8 and the histidine (H) at position 559 of the sequence of SEQ ID NO. 22. The substituents may be, without limitation, alanine. As used herein, the term "cleavage" refers to the breakage of the covalent backbone of a nucleotide molecule.

In some embodiments of the present disclosure, the Cas protein can be a recombinant protein. The term "recombinant", as used in conjunction with, for example, a cell, nucleic acid, protein, or vector, refers to the cell, nucleic acid, protein or vector that is modified by the introduction of a heterologous nucleic acid or protein or by the alteration of a native nucleic acid or protein, or which is derived from such a modified cell. Thus, for example, a recombinant Cas protein may be generated by reconstituting a Cas protein-encoding nucleic acid sequence (i.e., a sequence encoding a Cas protein), based on the human codon table.

In some embodiments of the present disclosure, the Cas protein or the nucleic acid encoding the same may be in a form that is allowed to be active within the nucleus.

In some embodiments of the present disclosure, the isolated Cas protein may be in a form that is easy to introduce into cells. For example, the Cas protein may be linked to a cell-penetrating peptide or a protein transduction domain. The protein transduction domain may be, without limitation, poly-arginine or an HIV-derived TAT protein. The present disclosure encompasses various examples of cell-penetrating peptides or protein transduction domains that are well known in the art.

In some embodiments of the present disclosure, the Cas protein or the nucleic acid encoding the same may further comprise a nuclear localization signal (NSL) for transporting the protein or nucleic acid into a nucleus in a cell by nuclear transport. In addition, the nucleic acid encoding the Cas protein may further comprise a nuclear localization signal (NLS) sequence. Thus, the Cas protein-encoding nucleic acid may be present as a component of an expression cassette that may contain, but is not limited to, an NLS sequence as well as a regulatory element, such as a promoter.

In some embodiments of the present disclosure, the Cas protein may be linked with a tag that facilitates separation and/or purification. As a non-limiting example, a small peptide tag, such as a His tag, a Flag tag, an S tag, etc., a glutathione S-transferase (GST) tag, or a maltose binding protein (MBP) tag may be used, depending on the purpose.

In some embodiments of the present disclosure, where the Cas protein is associated with target DNA-specific guide RNA, the Cas protein may be collectively termed an RGEN (RNA-Guided Engineered Nuclease). As used herein, the term "RGEN" refers to a nuclease having a target DNA-specific guide RNA and a Cas protein.

For application to cells, according to some embodiments of the present disclosure, the RGEN may have a target DNA-specific guide RNA or a DNA encoding the guide RNA; as well as an isolated Cas protein or a nucleic acid encoding the Cas protein. In this regard, the guide RNA or the DNA encoding the guide RNA may be applied to cells simultaneously or sequentially with the Cas protein or the nucleic acid encoding the Cas protein.

In an aspect of the present disclosure, the RGEN for delivery to cells include 1) a target DNA-specific guide RNA and an isolated Cas protein, or 2) a DNA encoding the guide RNA or a nucleic acid encoding the Cas protein. Delivery in the form of 1) is designated "RNP delivery." Examples of the isolated guide RNA may comprise, but are not limited to, in vitro transcribed RNAs.

In some embodiments of the present disclosure, the guide RNA-coding DNA (DNA encoding the guide RNA) and the Cas protein-coding nucleic acid may themselves be used as isolated nucleic acids. Alternatively, without limitation, they may be present in a vector having an expression cassette for expressing the guide RNA and/or the Cas protein. Examples of suitable vectors include a viral vector, a plasmid vector, and an agrobacterium vector. The viral vector may be exemplified by, but is not limited to, an AAV (adeno-associated virus).

In some embodiments of the present disclosure, without limitation, the guide RNA-coding DNA and the Cas protein-coding nucleic acid may be present separately in respective vectors or together in a single vector.

The foregoing application embodiments of the subject matter can be applied to more exemplary embodiments as described in this specification. In addition, application embodiments that will be described later may be applied in combination with other constitutional elements.

As used herein, the term "guide RNA" may refer to a RNA having specificity to a target DNA (i.e., a target DNA-specific RNA), which can be coupled with a Cas protein to guide the Cas protein to the target DNA.

Moreover, at least in some embodiments, the guide RNA may be designed to be specific for a certain target to be cleaved.

In some embodiments of the present disclosure, the guide RNA may be a dual RNA consisting of two RNAs, that is, a crRNA and a tracrRNA. In other embodiments, the guide RNA may be a sgRNA comprising or consisting of a first region containing a sequence complementary to the target DNA capable of forming a duplex with a complementary strand of the target DNA, and a second region containing a sequence responsible for interacting with the Cas protein. More particularly, the guide RNA may be a sgRNA (single guide RNA or single-stranded guide RNA) synthesized by fusing respective essential portions of a crRNA and a tracrRNA.

In some embodiments of the present disclosure, the sequence capable of forming a duplex with a complementary strand of a target DNA sequence in the guide RNA may range, without limitation, in length from 17 to 23 bp, from 18 to 23 bp, from 19 to 23 bp, particularly from 20 to 23 bp, and more particularly from 21 to 23 bp. The length may be applied to both the dual RNA and the sgRNA, and more particularly to the sgRNA.

In some embodiments of the present disclosure, the guide RNA may comprise one to three, more particularly two or three additional nucleotides just prior to the 5'end of the sequence capable of forming a duplex with a complementary strand of a target DNA sequence. The nucleotides are selected from among A, T, G, C, and combinations thereof. The guide RNA may comprise, as additional nucleotides, one to three consecutive guanine (G) residues, more preferably, two or three consecutive G residues. This is applied, without limitation, to both dualRNAs and sgRNAs, and more preferably to sgRNAs.

In some embodiments of the present disclosure, the sgRNA may comprise a region complementary to a target DNA sequence (termed "Spacer region", "Target DNA recognition sequence", "base pairing region", etc.), and a hairpin structure for binding to the Cas protein.

In some embodiments of the present disclosure, the sgRNA may comprise a region complementary to a target DNA sequence, a hairpin structure for binding to the Cas protein, and a terminator sequence. These elements may be, without limitation, sequentially arranged in the 5' to 3' direction.

In some embodiments of the present disclosure, any form of guide RNA can be used, as long as it contains respective essential portions of a crRNA and a tracrRNA and a region complementary to a target DNA.

In some embodiments of the present disclosure, the crRNA may hybridize with a target DNA.

In some embodiments of the present disclosure, the RGEN may consist of a Cas protein and a dualRNA, or a Cas protein and an sgRNA. Alternatively, the RGEN may comprise respective nucleic acids encoding a Cas protein and an sgRNA as constitutional elements, but is not limited thereto.

In some embodiments of the present disclosure, the guide RNA, e.g., crRNA or sgRNA, may contain a sequence complementary to a target DNA sequence, and may comprise one or more additional nucleotides located upstream of the crRNA or sgRNA, particularly at the 5' end of the crRNA of sgRNA or dualRNA. The additional nucleotides may be, but are not limited to, guanine (G) residues.

In some embodiments of the present disclosure, the guide RNA may comprise a sequence capable of forming a duplex with (i.e., forming a base pair with or hybridizing to) a complementary strand of a target DNA sequence adjacent to the PAM (proto-spacer-adjacent motif) sequence NNNNRYAC (SEQ ID NO: 1).

In some embodiments of the present disclosure, the guide RNA may comprise a first region, capable of forming a duplex with a complementary stand of a target DNA sequence, and a second region, comprising a stem-loop structure characterized by a stem 13-18 bp in length. In certain embodiments, the stem may comprise the nucleotide sequence of SEQ ID NO: 2 (5'-GUUUUAGUCCCUUGUG-3') and a complementary sequence thereof.

In some embodiments of the present disclosure, the guide RNA may comprise a first region, capable of forming a duplex with a complementary stand of a target DNA sequence, and a second region comprising a stem-loop structure characterized by a loop 5-10 bp in length. The loop may comprise the nucleotide sequence of SEQ ID NO: 3 (5'-AUAUUCAA-3').

In some embodiments of the present disclosure, the Cas proteins and the guide RNAs, especially sgRNAs, which are described above or later, may be those that are not naturally occurring or are engineered. In addition, the factors described for each matter may be combined together for application.

In some embodiments of the present disclosure, the intracellular introduction of RGEN can be achieved by, but is not limited to, (1) delivering the Cas9 protein, purified after bacterial overexpression, and the sgRNA (single guided RNA), that recognizes a specific HLA target sequence, which is prepared after in vitro transcription in cells, or (2) delivering a plasmid carrying the Cas9 gene and the sgRNA into cells for expression or transcription.

In addition, proteins, RNAs or plasmid DNAs encompassed within the scope of the present disclosure can be introduced into cells through various methods known in the art, such as, without limitation, electroporation, or techniques using liposomes, viral vectors, nanoparticles, or PTD (protein translocation domain) fusion proteins.

In some embodiments, a method of the present disclosure may be used to cleave a target DNA comprising the PAM sequence of SEQ ID NO: 1, and more particularly to edit a genome. In this context, the Cas protein may be in an active form with a nuclease or nickase activity.

In certain embodiments, the Cas protein may be in a deactivated (inactivated) form. In this case, the method of the present disclosure is conducted in such a way that a target DNA sequence comprising the PAM sequence of SEQ ID NO: 1 is not cleaved, but is associated with the Cas protein.

Moreover, in some other embodiments, the Cas protein, more particularly, the deactivated Cas protein, may further comprise a transcription effector domain. In detail, the deactivated Cas protein may be linked to, without limitation, an activator, a repressor, or so on.

Given the transcription effector domain, the method, at least in some embodiments, may be applied to Cas-mediated gene expression regulation comprising transcriptional regulation or epigenetic regulation.

In accordance with another aspect, the present disclosure provides an isolated guide RNA comprising a sequence capable of forming a duplex with a complementary strand of a target DNA sequence adjacent to the PAM (proto-spacer-adjacent motif) NNNNRYAC (SEQ ID NO: 1). The isolated guide RNA may be one that is not naturally occurring or is artificially engineered. The individual elements are as described above.

In some embodiments of the present disclosure, the guide RNA may be single guide RNA in which the sequence capable of forming a duplex with a complementary strand of a target DNA may range in length from 17 to 23 bp, from 18 to 23 bp, from 19 to 23 bp, particularly from 20 to 23 bp, and more particularly from 21 to 23 bp, without being limited thereto.

Further, the guide RNA, at least in some embodiments, may comprise one to three consecutive guanine (G) residues just upstream of the 5'end of the complementary strand of the target DNA, but is not limited thereto. Additionally, the foregoing description of the additional nucleotides can also be applicable to this embodiment.

Also, provided in accordance with a another aspect of the present disclosure is a composition comprising a guide RNA comprising a sequence capable of forming a duplex with a complementary strand of a target DNA sequence adjacent to the PAM (proto-spacer-adjacent motif) sequence NNNNRYAC (SEQ ID NO: 1), or a DNA encoding the guide RNA. Each of the components, in at least some embodiments, is as described above.

In some embodiments of the present disclosure, the composition may further comprise a Cas protein recognizing the sequence NNNNRYAC (SEQ ID NO: 1) or a nucleic acid encoding the Cas protein.

In addition, in certain embodiments, the composition may be used for genome editing.

Further, in some embodiments, the composition may comprise: (i) a guide RNA comprising a sequence capable of forming a duplex with a complementary strand of a target DNA sequence adjacent to the PAM (proto-spacer-adjacent motif) NNNNRYAC (SEQ ID NO: 1), or a DNA encoding the guide RNA; and (ii) an deactivated Cas protein (dCas) or a nucleic acid encoding the dCas.

In an embodiment, the deactivated Cas protein may further comprise a transcription effector domain.

In some embodiments of the present disclosure, the composition may be used to isolate a DNA of interest comprising a target DNA sequence. In this regard, the deactivated Cas protein may be labeled with a tag useful for separation and purification, but is not limited thereto. The tag may be as described above.

In some embodiments of the present disclosure, the composition may be used for Cas-mediated gene expression regulation, comprising transcriptional regulation or epigenetic regulation.

In some embodiments of the present disclosure, the target DNA may be present in isolated cells, for example, eukaryotic cells. Examples of the eukaryotic cells include yeasts, fungi, protozoa, cells from plants, higher plants, insects or amphibians, and mammalian cells such as CHO, HeLa, HEK293, and COS-1 cells. Without limitation, cultured cells (in vitro), graft cells, primary cell culture (in vitro and ex vivo), in vivo cells, and mammalian cells including human cells are commonly used in the art.

In accordance with a still further aspect, the present disclosure provides a CRISPR-CAS system, comprising (i) a guide RNA comprising a sequence capable of forming a duplex with a target DNA sequence adjacent to the PAM (proto-spacer-adjacent motif) NNNNRYAC (SEQ ID NO: 1), or a DNA encoding the guide RNA; and (ii) a Cas protein recognizing the PAM sequence NNNNRYAC (SEQ ID NO: 1) or a nucleic acid encoding the Cas protein. The individual factors are as described above. These factors may be non-naturally occurring or engineered.

Still another aspect of the present disclosure pertains to a recombinant viral vector, comprising (i) an expression cassette for a guide RNA comprising a sequence capable of forming a duplex with a target DNA sequence adjacent to the PAM (proto-spacer-adjacent Motif) sequence of NNNNRYAC (SEQ ID NO: 1), and (ii) an expression cassette for a Cas protein recognizing the PAM sequence of NNNNRYAC (SEQ ID NO: 1). The individual factors are as described above. These factors may be non-naturally occurring or engineered. The viral vector, at least in some embodiments, may be of AAV (Adeno-associated virus) origin.

Yet another aspect of the present disclosure pertains to an isolated guide RNA comprising a sequence of 21-23 bp in length, capable of forming a duplex with a complementary strand of a target DNA sequence. The guide RNA is as defined above. The guide RNA may be non-naturally occurring or engineered.

Yet still another aspect of the present disclosure pertains to a composition comprising the guide RNA or a DNA encoding the guide RNA. The individual factors are as described above. These factors may be non-naturally occurring or engineered.

The composition, at least in some embodiments, may comprise a Cas protein that recognizes the PAM sequence NNNNRYAC (SEQ ID NO: 1), or a nucleic acid that encodes the Cas protein.

In addition, the composition, in some embodiments, may comprise a deactivated Cas recognizing the NNNNRYAC sequence (SEQ ID NO: 1), or a nucleic acid encoding the deactivated Cas protein. The deactivated Cas protein, in some embodiments, may further comprise a transcription effector domain.

According to an additional aspect, the present disclosure provides an isolated guide RNA, comprising a first region comprising a sequence capable of forming a duplex with a complementary strand of a target DNA sequence, and a second region comprising a stem-loop structure characterized by a stem 13-18 bp in length. The individual factors are as defined above. These factors may be non-naturally occurring or engineered.

In certain embodiments, the stem may comprise the nucleotide sequence of SEQ ID NO: 2 (5'-GUUUUAGUC-CCUUGUG-3') and a complementary sequence thereof.

According to a further additional aspect, the present disclosure provides an isolated guide RNA, comprising a first region comprising a sequence capable of forming a duplex with a complementary strand of a target DNA sequence, and a second region comprising a stem-loop structure characterized by a loop 5-10 bp in length. The individual factors are as defined above. These factors may be non-naturally occurring or engineered.

In certain embodiments, the loop may comprise the nucleotide sequence of SEQ ID NO: 3 (5'-AUAUUCAA-3').

According to yet an additional aspect, the present disclosure provides a composition comprising a guide RNA, along with a Cas protein or a nucleic acid encoding the Cas protein. The individual factors are as defined above. These factors may be non-naturally occurring or engineered.

Yet still another aspect of the present disclosure provides a method for genome editing in a cell, comprising introducing into the cell an isolated guide RNA or a DNA encoding the isolated guide RNA, together with a Cas protein or a nucleic acid encoding the Cas protein. The individual factors are as defined above. These factors may be non-naturally occurring or engineered.

Yet a further aspect of the present disclosure provides a method for cleaving a target DNA in a cell, comprising introducing into the cell an isolated guide RNA or a DNA encoding the isolated guide RNA, along with a Cas protein or a nucleic acid encoding the Cas protein. The individual factors are as defined above. These factors may be non-naturally occurring or engineered.

In certain embodiments, the guide RNA or the DNA encoding the guide RNA may be introduced into a cell simultaneously or sequentially with the Cas protein or the nucleic acid encoding the Cas protein.

A still further aspect of the present disclosure provides a method for preparing a target DNA-recognizing sequence of a guide RNA (i.e., a sequence in a guide RNA that is responsible for recognizing a target DNA), comprising: (i) identifying the presence of a PAM sequence NNNNRYAC (SEQ ID NO: 1) in a given sequence; and (ii) determining a sequence located just upstream of the PAM sequence NNNNRYAC (SEQ ID NO: 1) as being recognizable by a guide RNA, if the presence of the PAM sequence is identified in step (i). The individual factors are as defined above. These factors may be non-naturally occurring or engineered.

In some embodiments of the disclosure, the sequence located upstream of the PAM sequence may range, without limitation, in length from 17 to 23 bp, from 18 to 23 bp, from 19 to 23 bp, more particularly from 20 to 23 bp, and even more particularly from 21 to 23 bp.

Yet another aspect of the present disclosure provides a method for isolating a DNA of interest, comprising: (i) introducing into a cell a guide RNA or a DNA encoding the guide RNA, along with a deactivated Cas protein or a nucleic acid encoding the deactivated Cas protein, thereby permitting the guide RNA and the deactivated Cas protein to form a complex together with the DNA of interest comprising a target DNA sequence; and (ii) separating the complex from a sample. The individual factors are as defined above. These factors may be non-naturally occurring or engineered. The deactivated Cas protein, at least in some embodiments, may recognize the PAM (protospacer-adjacent Motif) sequence NNNNRYAC (SEQ ID NO: 1).

In certain embodiments, the method for isolating a DNA of interest may be performed by allowing a guide RNA (gRNA), binding specifically to the DNA of interest, and a deactivated Cas protein (dCas) to form a dCas-gRNA-DNA of interest complex with the DNA of interest; and separating the complex from a sample. The DNA of interest, in some embodiments, may be identified using a well-known detection method, such as PCR amplification, etc. The isolation method, in some embodiments, may be adapted for cell-free DNA in vitro without forming crosslinks via covalent bonds between the DNA, the gRNA, and the dCas. In addition, the isolation method may further comprise isolating the DNA of interest from the complex in some embodiments.

The deactivated Cas protein, in some embodiments, may be linked with an affinity tag for use in isolating the DNA of interest. The affinity tag may be selected from the group consisting of a His tag, a Flag tag, an S tag, a GST (Glutathione S-transferase) tag, an MBP (Maltose binding protein) tag, a CBP (chitin binding protein) tag, an Avi tag, a calmodulin tag, a polyglutamate tag, an E tag, an HA tag, a myc tag, an SBP tag, softag 1, softag 3, a strep tag, a TC tag, an Xpress tag, a BCCP (biotin carboxyl carrier protein) tag, and a GFP (green fluorescent protein) tag, but are not limited thereto. The deactivated Cas protein, in some embodiments, may be a Cas protein that lacks DNA cleavage activity.

Isolation of a DNA of interest, in some embodiments, may be achieved using an affinity column or magnetic beads capable of binding the tag used. For example, when a His tag is used to isolate the DNA of interest, a metal affinity column or magnetic beads capable of binding the His tag may be employed. The magnetic beads may comprise, but are not limited to, Ni-NTA magnetic beads.

In some embodiments, isolation of a DNA of interest from the complex may be conducted using RNase and protease.

In some embodiments in the method for isolating a DNA of interest, a certain genotype DNA, or two or more different DNAs of interest can be isolated from an isolated sample containing a mixture of two or more different genotype DNAs. When the method involves isolating two or more different DNAs of interest, guide RNAs respectively specific for the two or more different DNAs of interest may be employed to isolate two or more DNAs of interest.

In certain embodiments, the guide RNA may be single guide RNA (sgRNA), or dualRNA comprising crRNA and tracrRNA. The guide RNA may be an isolated RNA, or may be encoded in a plasmid.

The isolation method, in certain embodiments, may be performed by binding a guide RNA (gRNA) specifically to 1) a DNA of interest and 2) a deactivated Cas protein (dCas) to form a dCas-gRNA-DNA complex with the DNA of interest; and separating the complex from the sample.

Yet an additional aspect of the present disclosure provides a method for Cas-mediated gene expression regulation in a DNA of interest comprising a target DNA sequence, the method comprising introducing an isolated guide RNA, specifically recognizing the target DNA or a DNA encoding the guide RNA, along with a deactivated Cas protein fused to a transcription effector domain or a nucleic acid encoding the deactivated Cas protein, into a cell. The individual factors are as defined above. These factors may be non-naturally occurring or engineered.

EXAMPLES

The following examples are provided for the purpose of illustrating some aspects of the disclosure provided herewith and they should not be construed as limiting the scope of the present disclosure in any manner.

C. jejuni CRISPR/Cas9 System

Example 1: Genome Editing Using C. jejuni CRISPR/Cas9

The present inventors succeeded in isolating RGEN from C. jejuni. To identify the characteristics of the C. jejuni CRISPR/CAS9-derived RGEN with regard to genome editing, a C. jejuni CAS9 gene optimized for human codons was synthesized (TABLE 1) and then inserted into a mammalian expression vector to construct a C. jejuni CAS9 expression cassette in which the HA-tagged, NLS-linked Cas gene was under the regulation of a CMV promoter (FIG. 1).

TABLE 1

Amino Acid Sequence of C. jejuni Cas9 Protein

| Amino acid sequence | size | SEQ ID NO |
|---|---|---|
| MARILAFDIGISSIGWAFSENDELKDCGVRIFTKVENPKTGESLALPRRLA RSARKRLARRKARLNHLKHLIANEFKLNYEDYQSFDESLAKAYKGSLIS PYELRFRALNELLSKQDFARVILHIAKRRGYDDIKNSDDKEKGAILKAIK QNEEKLANYQSVGEYLYKEYFQKFKENSKEFTNVRNKKESYERCIAQSF LKDELKLIFKKQREFGFSFSKKFEEEVLSVAFYKRALKDFSHLVGNCSFF TDEKRAPKNSPLAFMFVALTRIINLLNNLKNTEGILYTKDDLNALLNEVL KNGTLTYKQTKKLLGLSDDYEFKGEKGTYFIEFKKYKEFIKALGEHNLS QDDLNEIAKDITLIKDEIKLKKALAKYDLNQNQIDSLSKLEFKDHLNISFK ALKLVTPLMLEGKKYDEACNELNLKVAINEDKKDFLPAFNETYYKDEV TNPVVLRAIKEYRKVLNALLKKYGKVHKINIELAREVGKNHSQRAKIEK EQNENYKAKKDAELECEKLGLKINSKNTLKLRLFKEQKEFCAYSGEKIKI SDLQDEKMLEIDHIYPYSRSFDDSYMNKVLVFTKQNQEKLNQTPFEAFG NDSAKWQKIEVLAKNLPTKKQKRILDKNYKDKEQKNFKDRNLNDTRYI ARLVLNYTKDYLDFLPLSDDENTKLNDTQKGSKVHVEAKSGMLTSALR HTWGFSAKDRNNHLHHAIDAVIIAYANNSIVKAFSDFKKEQESNSAELY AKKISELDYKNKRKFFEPFSGFRQKVLDKIDEIFVSKPERKKPSGALHEET FRKEEEFYQSYGGKEGVLKALELGKIRKVNGKIVKNGDMFRVDIFKHK KTNKFYAVPIYTMDFALKVLPNKAVARSKKGEIKDWILMDENYEFCFSL YKDSLILIQTKDMQEPEFVYYNAFTSSTVSLIVSKHDNKFETLSKNQKILF KNANEKEVIAKSIGIQNLKVFEKYIVSALGEVTKAEFRQREDFKKSGPPK KKRKVYPYDVPDYA- | 1003 a.a | 22 |

The native guide RNA of the C. jejuni CRISPR/CAS9 system consists of tracrRNA and target-specific crRNA. In view of the notion that the guide RNA is used as the two RNA molecules in themselves or as a single guide RNA (sgRNA) in which crRNA and tracrRNA are fused to each other, the present inventors designed and constructed an expression plasmid for C. jejuni sgRNA (TABLE 2).

TABLE 2

| sgRNAs | sgRNA sequence | SEQ ID NO |
|---|---|---|
| C. jejuni_ sgRNA | NNNNNNNNNNNNNNNNNNNNGTTTTAGTCCCT GAAAAGGGACTAAAATAAAGAGTTTGCGGGAC TCTGCGGGGTTACAATCCCCTAAAACCGCTTT TTTT | 23 |

Then, potential target loci for human AAVS1 and mouse Rosa-26 were selected based on the PAM sequence (NN-NACA) of the *C. jejuni* CRISPR/CAS9 system (TABLE 3).

TABLE 3

| sgRNAs | Target Sequence | SEQ ID NO |
|---|---|---|
| Human AAVS1_ C. Jejuni | ATATAAGGTGGTCCCAGCTCGGGGACA | 24 |
| Mouse Rosa26_ C. Jejuni | ATTCCCCTGCAGGACAACGCCCACACA | 25 |

To examine whether the *C. jejuni* RGEN can be used for the targeted disruption of endogenous genes in mammalian cells, genomic DNA, isolated from transfected cells using T7 endonuclease I (T7E1), a mismatch-sensitive endonuclease that specifically recognizes and cleaves heteroduplexes formed by the hybridization of wild-type and mutant DNA sequences, was analyzed. The primer sequences used are as follows (TABLE 4).

TABLE 4

| Primer | Sequence | SEQ ID NO |
|---|---|---|
| Human AAVS1-F | TGCTTCTCCTCTTGGGAAGT | 26 |
| Human AAVS1-R | CCCCGTTCTCCTGTGGATTC | 27 |
| Mouse Rosa26-F | ACGTTTCCGACTTGAGTTGC | 28 |
| Mouse Rosa26-R | CCCAGCTACAGCCTCGATTT | 29 |

Figure 2A:
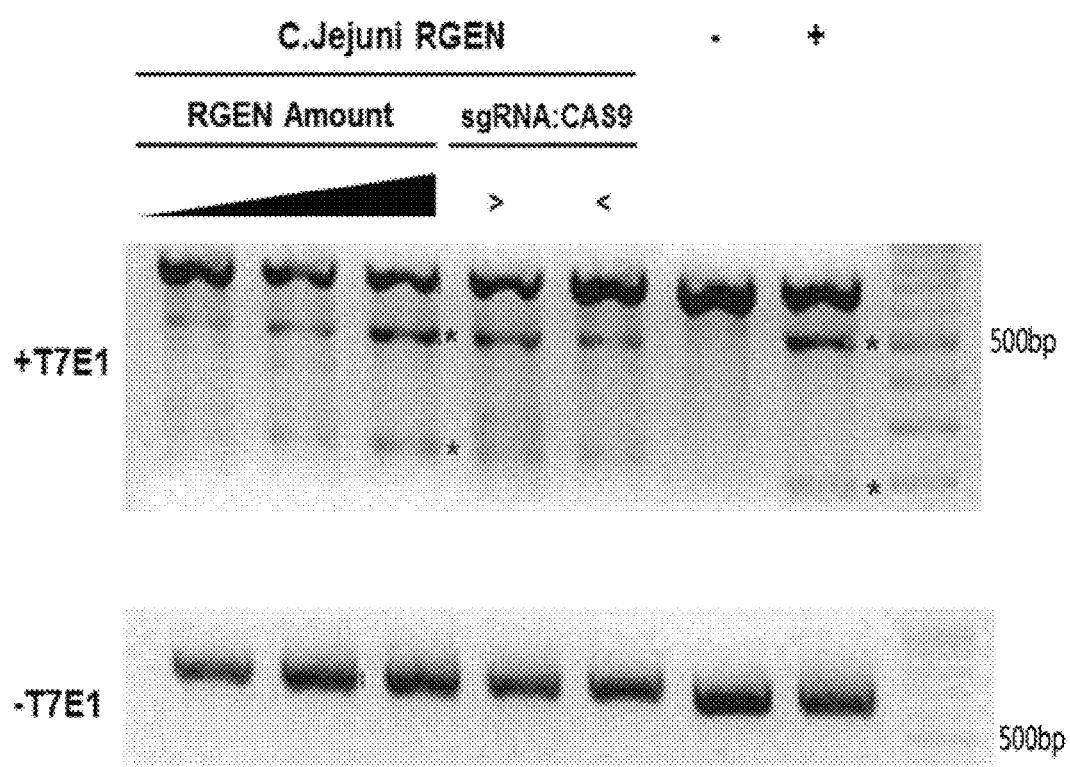

As a result, mutations (interchangeably substitution or variation) were detected only in the cells into which the CAS9 protein and the guide RNA were introduced together. The mutation frequency was found to be RNA-dose dependent, as measured based on relative DNA band intensities (FIG. 2A). In addition, DNA sequencing analysis of the PCR amplicons corroborated the induction of RGEN-mediated mutations at the endogenous sites. Indels and microhomologies, which are characteristic of error-prone nonhomologous end joining (NHEJ) repair, were observed at the target sites (FIG. 2B). The mutation frequency was 16.7% as measured by direct sequencing (=2 mutant clones/12 clones).

Figure 3A:
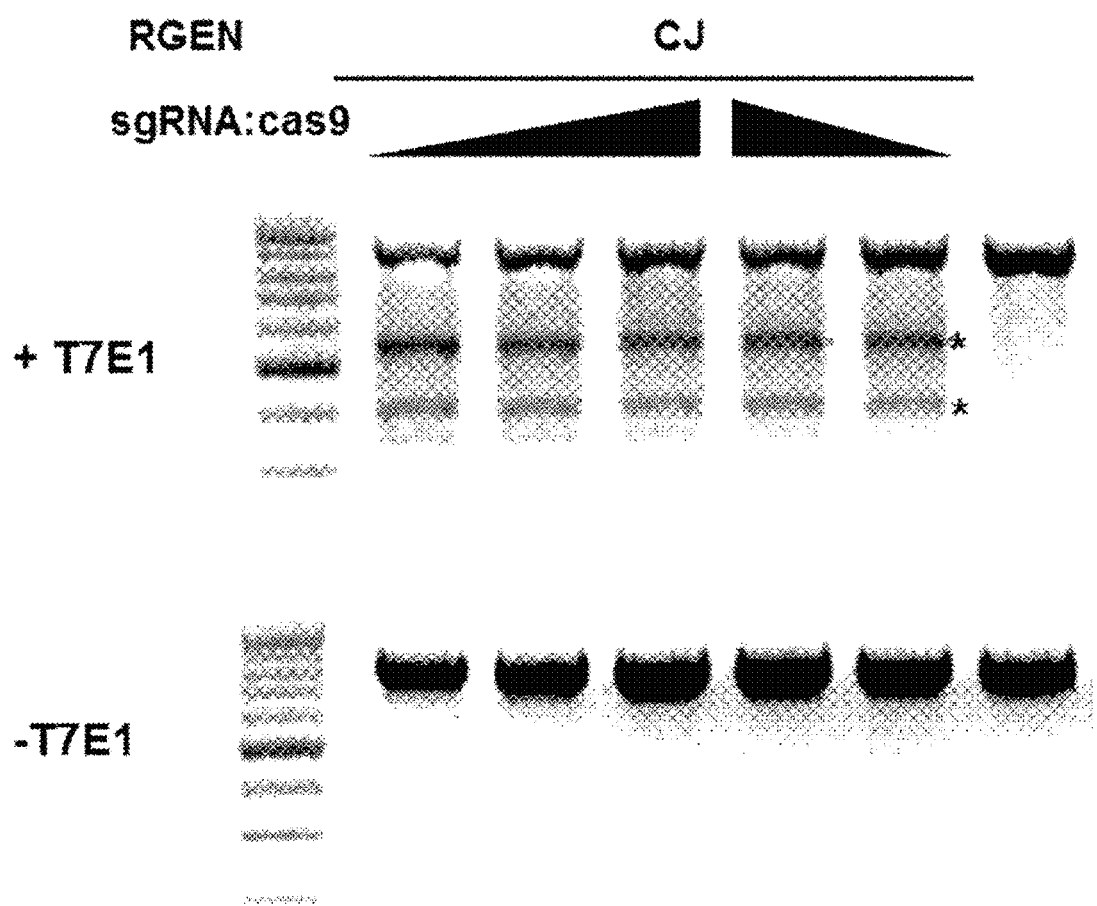

Likewise, when mouse Rosa26 *C. jejuni* RGEN was delivered into mouse NHI3T3 cells, mutations were effectively induced at the mouse Rosa26 site, as measured by a T7E1 assay (FIG. 3A). In addition, DNA sequencing analysis of the PCR amplicons revealed the induction of *C. jejuni* RGEN-mediated mutation at the endogenous gene sites (FIG. 3B). The mutation frequency was found to be 22.2% as measured by direct sequencing (2 mutant clones/9 clones).

Example 2: Structural Modification of sgRNA

With the anticipation that the *C. jejuni* crRNA:tracrRNA complex would comprise a shorter loop structure than those from other bacterial species, a modified stem or loop structure was designed to structurally stabilize the *C. jejuni* RGEN sgRNA constructed in Example 1 (TABLE 5).

TABLE 5

| sgRNAs | sgRNA Sequecne | SEQ ID NO |
|---|---|---|
| C. jejuni_ sgRNA | NNNNNNNNNNNNNNNNNNNNGTTTTAGTCCC TGAAAAGGGACTAAAATAAAGAGTTTGCGGG ACTCTGCGGGGTTACAATCCCCTAAAACCGCTT TTTTT | 23 |
| C. jejuni_ sgRNA_stem modified | NNNNNNNNNNNNNNNNNNNNGTTTTAGTCCC TTGTGGAAATATAAGGGACTAAAATAAAGAG TTTGCGGGACTCTGCGGGGTTACAATCCCCTAA AACCGCTTTTTT | 30 |
| C. jejuni_ sgRNA_loop modified | NNNNNNNNNNNNNNNNNNNNGTTTTAGTCCC TATATTCAAAGGGACTAAAATAAAGAGTTTGC GGGACTCTGCGGGGTTACAATCCCCTAAAACC GCTTTTTT | 31 |

In TABLE 5, norm stem parts are shown in bold and underlined.

Figure 4:
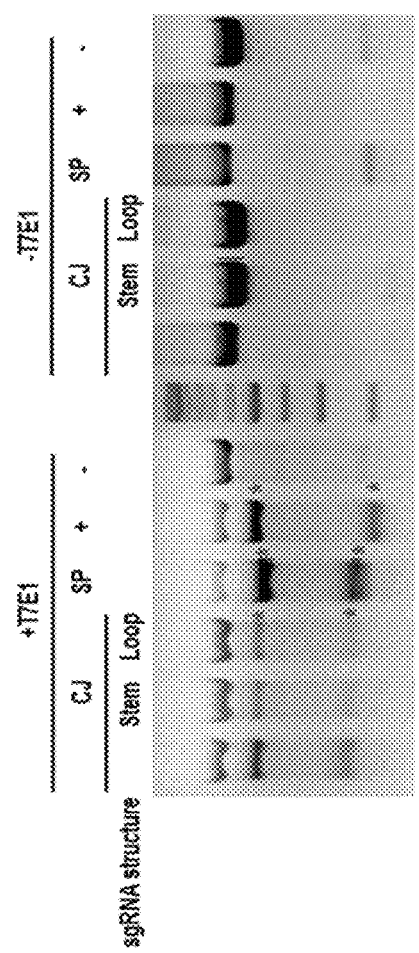
FIG. 4 shows certain mutations induced in endogenous AAVS1 target loci by a mutant *C. jejuni* sgRNA structure. RGEN-driven chromosomal mutations were detected using a T7E1 assay. Asterisks (*) indicate DNA bands that are anticipated to be cleaved by T7E1. HEK293 wt gDNA was used as a negative control (−). A previously proven RGEN was used as a positive control (+).

When the modified sgRNA was introduced to target the target site of the human AAVS1 *C. jejuni* RGEN into which mutations were successfully induced through the normal sgRNA structure, similar mutation frequencies were observed (FIG. 4). In this regard, the primer sequences used are as shown in TABLE 4.

Example 3: Optimization of Length of sgRNA Spacer

The spacer sequence of *C. jejuni* crRNA, recognizing a target sequence, was reported to be 20 bp in length in the literature. To determine which spacer length is optimal, a genome editing test was performed for 4 target sites of Cj Cas9 on human AAVS1 loci, as shown in TABLE 6, using spacers with various lengths, and sgRNA mutant structures with additional nucleotides at 5' terminus (FIGS. 5A to 5C). For the method used in this experiment, reference was made to Genome Res. 2014 January; 24(1):132-41.

TABLE 6

Target Site

| sgRNA | Sequence (20 bp-SPACERnnnnACA) | SEQ ID NO |
|---|---|---|
| Human AAVS1-CJ1 | ATATAAGGTGGTCCCAGCTCggggACA | 32 |
| Human AAVS1-NRG1 | GTAGAGGCGGCCACGACCTGgtgaACA | 33 |
| Human AAVS1-NRG3 | TCACAAAGGGAGTTTTCCACacggACA | 34 |
| Human AAVS1-NRG5 | TAGGCAGATTCCTTATCTGGtgacACA | 35 |

Three days after an sgRNA expression vector was delivered into 293-cells, genomic DNA was isolated and analyzed for mutation efficiency by deep sequencing. The results are depicted in FIG. 5C. As can be seen, high efficiency was detected when the spacers ranged in length from 21 to 23 bp. In addition, even when 2-3 additional G residues were added to the 5' end of sgRNA of a 20 bp-long spacer, an improvement in genome editing was observed.

TABLE 7

| NGS-primer-F* | Sequences | NGS-primer-R** | Sequences | Target sgRNA |
|---|---|---|---|---|
| HumanAS-AV-F1 AAVS1 | ACACTCTTTCCCTAC ACGACGCTCTTCCGA TCTAGGAGGAGGCCT AAGGATGG (SEQ ID NO: 36) | AS-AV-R1 | GTGACTGGAGT TCAGACGTGTG CTCTTCCGATCT TGTCATGGCATC TTCCAGGG (SEQ ID NO: 39) | CJ1 |
| AS-AV-F2 | ACACTCTTTCCCTAC ACGACGCTCTTCCGA TCTGCTCTGGGCGGA GGAATATG (SEQ ID NO: 37) | AS-AV-R2 | GTGACTGGAGT TCAGACGTGTG CTCTTCCGATCT TCCGTGCGTCAG TTTTACCT (SEQ ID NO: 40) | NRG1, NRG3 |
| AS-AV-F4 | ACACTCTTTCCCTAC ACGACGCTCTTCCGA TCTATCCTCTCTGGC TCCATCGT (SEQ ID NO: 38) | AS-AV-R4 | GTGACTGGAGT TCAGACGTGTG CTCTTCCGATCT CCGGTTAATGTG GCTCTGGT (SEQ ID NO: 41) | NRG5 |

Here, F* indicates a forward primer and R** indicates a reverse primer.

Example 4: *C. jejuni* Cas9 PAM Sequence Analysis

In the present disclosure, the PAM sequence of *C. jejuni* Cas9 was inferred to comprise "NNNNACA", based on data in the existing literature, and experiments were conducted. Of 34 *C. jejuni* CRISPR/Cas9 systems constructed for five genome sites, only three exhibited activity. Particularly, additional analysis of the sequences covering the sites in the three active systems showed that the nucleotide "C" was identified immediately after the PAM sequence (NNN-NACA) in all three sites (TABLE 8).

TABLE 8

| | sgRNA | Activity (T7E1 assay) | Sequence | SEQ ID NO |
|---|---|---|---|---|
| Human | | | | |
| AAVS1 | hAAVS1-CJ1 | O | ATATAAGGTGGTCCCAGCTCGGG GACAC | 42 |
| | hAAVS1-CJ2 | X | TGGCCCCACTGTGGGGTGGAGGGGA CAG | 43 |
| | hAAVS1-CJ3 | X | CACCCCACAGTGGGGCCACTAGGGA CAG | 44 |
| CCR5 | CCR-CJ1 | X | CTAGCAGCAAACCTTCCCTTCACTAC AA | 45 |
| | CCR5-CJ2 | X | CTCCATGAATGCAAACTGTTTTATAC AT | 46 |
| | CCR5-CJ3 | X | TGCATTCATGGAGGGCAACTAAATA CAT | 47 |
| | CCR5-CJ4 | X | ATCAAGTGTCAAGTCCAATCTATGA CAT | 48 |
| | CCR5-CJ5 | X | CCAATCTATGACATCAATTATTATAC AT | 49 |
| | CCR5-CJ6 | X | GCAAAAGGCTGAAGAGCATGACTG ACAT | 50 |
| | CCR5-CJ7 | X | GCAGCATAGTGAGCCCAGAAGGGG ACAG | 51 |
| | CCR5-CJ8 | X | GCCGCCCAGTGGGACTTTGGAAATA CAA | 52 |
| Mouse | | | | |
| Rosa26 | ROSA26-CJ1 | X | TCCACTGCAGCTCCCTTACTGATAAC AA | 53 |
| | ROSA26-CJ2* | O | ATTCCCCTGCAGGACAACGCCCAC ACAC | 54 |
| | ROSA26-CJ3 | X | ACACCTGTTCAATTCCCCTGCAGGA CAA | 55 |
| | ROSA26-CJ4 | X | TTGAACAGGTGTAAAATTGGAGGGA CAA | 56 |
| | ROSA26-CJ5 | X | TTGCCCCTATTAAAAAACTTCCCGAC AA | 57 |

TABLE 8-continued

| sgRNA | | Activity (T7E1 assay) | Sequence | SEQ ID NO |
|---|---|---|---|---|
| | ROSA26-CJ6 | X | AGATCCTTACTACAGTATGAAATTACAG | 58 |
| | ROSA26-CJ7 | X | AGCCTTATCAAAAGGTATTTTAGAACAC | 59 |
| TP53 | TP53-CJ1 | X | CGGGGCCCACTCACCGTGCACATAACAG | 60 |
| | TP53-CJ2 | X | GCCGTGTCCGCGCCATGGCCATCTACAA | 61 |
| | TP53-CJ3 | X | TGGCCATCTACAAGAAGTCACAGCACAT | 62 |
| | TP53-CJ4 | X | CCGAGTGTCAGGAGCTCCTGCAGCACAG | 63 |
| | TP53-CJ5 | X | CTCCCCGGGGCCCACTCACCGTGCACAT | 64 |
| | TP53-CJ6 | X | CCTGTGCAGTTGTGGGTCAGCGCCACAC | 65 |
| | TP53-CJ7 | X | GGTGTGGCGCTGACCCACAACTGCACAG | 66 |
| | TP53-CJ8 | O | TTCTTGTAGATGGCCATGGCGCGGACAC | 67 |
| | TP53-CJ9 | X | CGCCATGGCCATCTACAAGAAGTCACAG | 68 |
| PTEN | mPTEN-CJ1 | X | ACATCATCAATATTGTTCCTGTATACAC | 69 |
| | mPTEN-CJ2 | X | TGAATCCAAAAACCTTAAAACAAACAA | 70 |
| | mPTEN-CJ3 | X | TGCTTTGAATCCAAAAACCTTAAACAA | 71 |
| | mPTEN-CJ4 | X | AGCATAAAAACCATTACAAGATATACAA | 72 |
| | mPTEN-CJ5 | X | GTAGATGTGCTGAGAGACATTATGACAC | 73 |
| | mPTEN-CJ6 | X | GGCGGTGTCATAATGTCTCTCAGCACAT | 74 |
| | mPTEN-CJ7 | X | ATTTAACTGCAGAGGTATGTATAAACAT | 75 |

Figure 6:
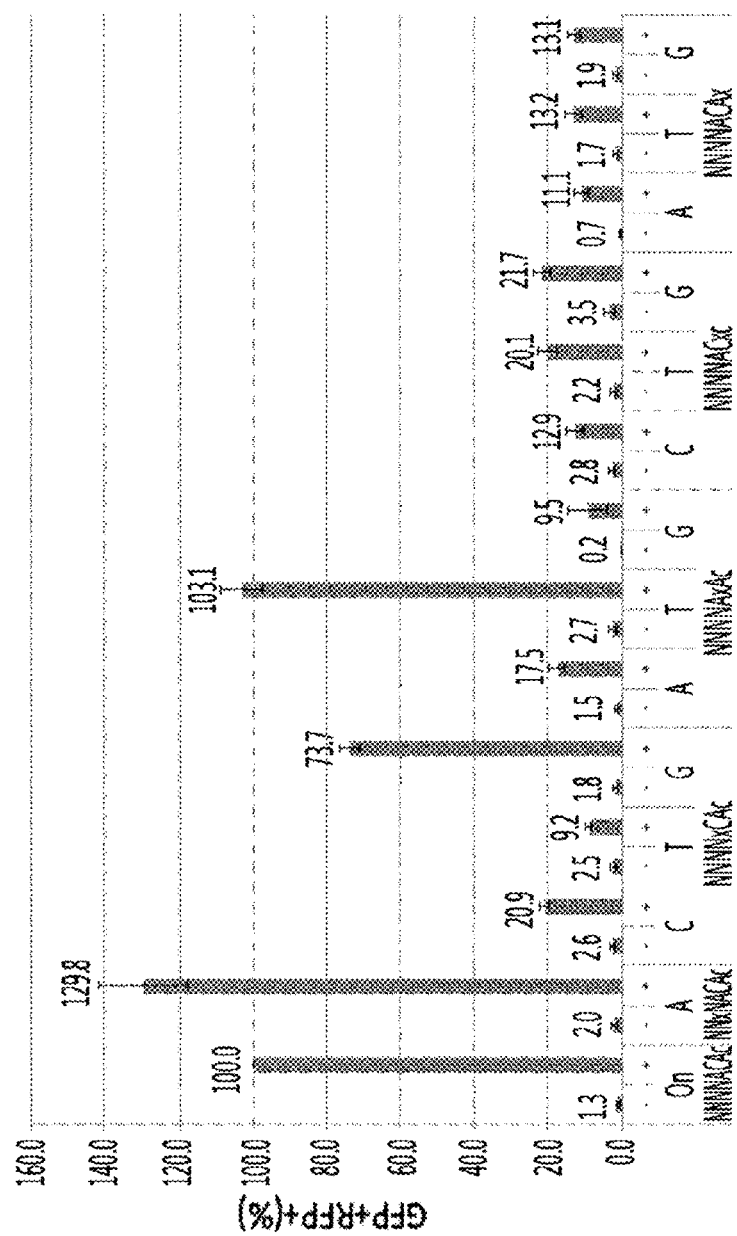
FIG. 6 is a graph showing the activity of *C. jejuni* CRISPR/Cas9 in which the AAVS1-CJ1 locus is inserted to a surrogate reporter. Relative to the activity (100) detected for the ACAC sequence at the PAM site, activities were calculated when different nucleotides were substituted at each position. At the first position, G as well as A guaranteed high activity. T as well as C were effective at the second position. However, only A and C exhibited activity at the third and fourth positions, respectively. Therefore, NNNN-A/G-C/T-A-C (or NNNNRYAC, SEQ ID NO: 1, wherein A/G=R, C/T=Y) is inferred to be an optimal PAM sequence at least in some embodiments.
Figure 7:
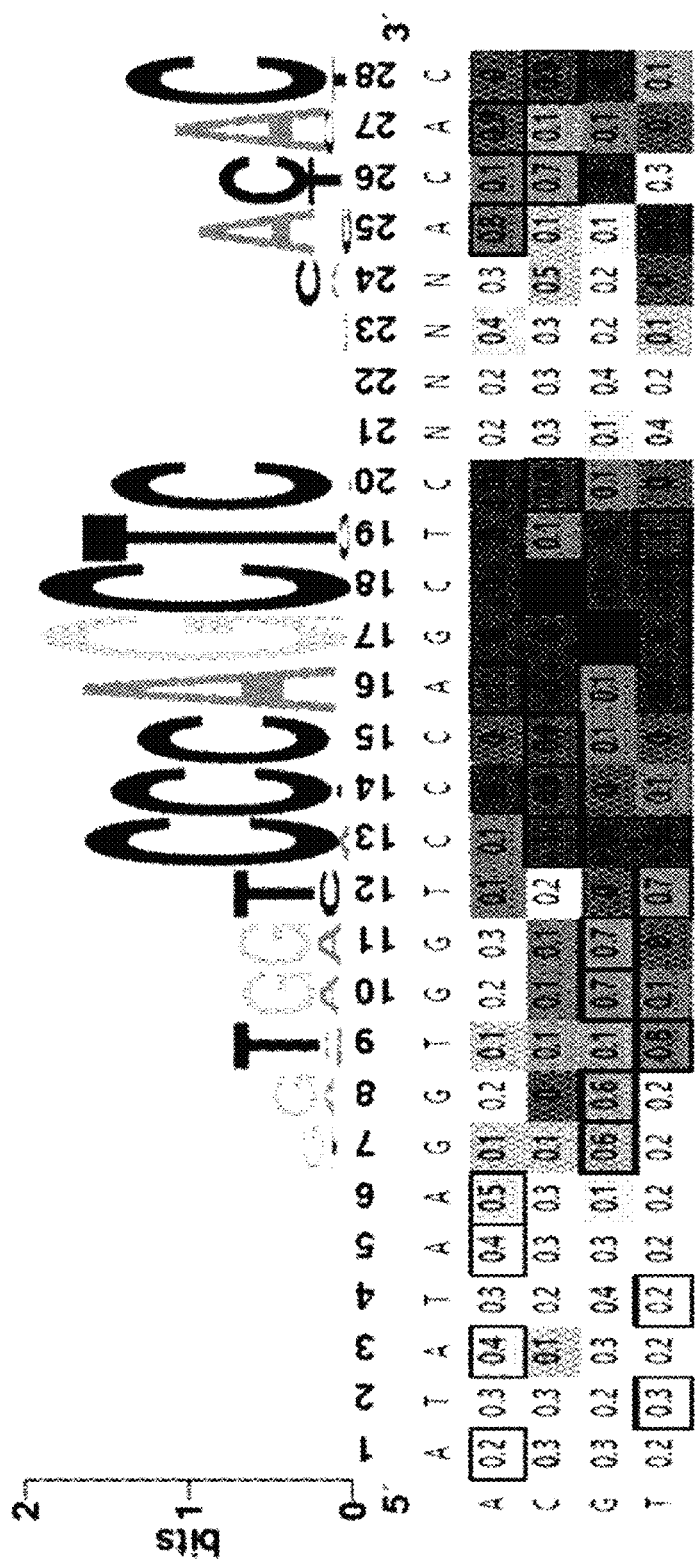
FIG. 7 shows a consensus logo for a potential off-target sequence of hAAVS1-CJ1 sgRNA, as excavated by the Digenome-Seq analysis.

Based on this result, the PAM sequence was inferred to contain "NNNNACAC". While the nucleotide at each site of "ACAC" were substituted by A/T/G/C, the activity of C. jejuni Cas9 was analyzed to identify the PAM sequence of C. jejuni RGEN. For this, a surrogate reporter assay was utilized. As a result, C. jejuni was identified to comprise the PAM sequence of "NNNNRYAC (SEQ ID NO: 1)" (FIG. 6, wherein R is a purine residue (A or G) and Y is a pyrimidine residue (C/T)). This experiment was carried out using the surrogate reporter assay described in Nat Methods. 2011 Oct. 9; 8(11):941-3.

Example 5: Assay of Specificity and PAM Sequence of C. jejuni CRISPR/Cas9

The cleavage sites of C. jejuni CRISPR/CAS9 in the AAVS1-CJ1 loci were analyzed at the genomic level using Digenome-seq, a CRISPR/Cas9 off-target assay developed and submitted for patent protection by the present inventors. The experiment was carried out using a method described in Nat Methods. 2015 March; 12(3):237-43.

Through Digenome-Seq, 41 loci at which AAVS1-CJ1 CRISPR/Cas9 seemed to be cleaved were determined (Genomic locations in TABLE 9). Consensus sequences were obtained from alignments of cleavage site sequences of the 41 loci, and PAM consistent with that identified in Example 4 was verified.

Further, to examine whether an off-target mutation is actually introduced into the potential off-targets acquired by Digenome-Seq, genomic DNA from 293-cells to which AAVS1-CJ1 CRISPR engineered nuclease was delivered was subjected to deep sequencing for 40 potential off-target sites. As shown in TABLE 9, no significant mutations were observed.

TABLE 9

| | | | Indel Frequency | |
|---|---|---|---|---|
| | Genomic Location | | Mock | C. Jejuni CRISPR |
| On-target | chr19 | 55627221 | 0.02 | 5.123 |
| CJ_AAVS1_1 | chr1 | 24521012 | 0.019 | 0.034 |
| CJ_AAVS1_2 | chr1 | 29848565 | 0.157 | 0.136 |
| CJ_AAVS1_3 | chr1 | 30381084 | 0.041 | 0.035 |
| CJ_AAVS1_4 | chr1 | 37283269 | 0.016 | 0.016 |
| CJ_AAVS1_5 | chr2 | 55333369 | 0.079 | 0.091 |
| CJ_AAVS1_6 | chr4 | 153532801 | 0.003 | 0.003 |
| CJ_AAVS1_7 | chr4 | 153926891 | 0 | 0 |
| CJ_AAVS1_8 | chr4 | 183304101 | 0.033 | 0.046 |
| CJ_AAVS1_9 | chr6 | 51746466 | 0.41 | 0.43 |
| CJ_AAVS1_10 | chr7 | 11346020 | 0.02 | 0.038 |
| CJ_AAVS1_11 | chr7 | 128481430 | 0.024 | 0.036 |
| CJ_AAVS1_12 | chr7 | 142878579 | 0.024 | 0.028 |
| CJ_AAVS1_13 | chr8 | 25979587 | 0.138 | 0.155 |
| CJ_AAVS1_14 | chr8 | 80240626 | 0.043 | 0.049 |
| CJ_AAVS1_15 | chr8 | 141347249 | 0.028 | 0.024 |
| CJ_AAVS1_16 | chr8 | 141688584 | 0.088 | 0.092 |
| CJ_AAVS1_17 | chr8 | 143120119 | 0.016 | 0.013 |
| CJ_AAVS1_18 | chr9 | 83960768 | 0.032 | 0.037 |
| CJ_AAVS1_19 | chr9 | 102650644 | 0.029 | 0.034 |
| CJ_AAVS1_20 | chr9 | 129141695 | 0.014 | 0.009 |
| CJ_AAVS1_21 | chr10 | 103862556 | 0.053 | 0.073 |
| CJ_AAVS1_22 | chr12 | 9085293 | 0.21 | 0.277 |
| CJ_AAVS1_23 | chr14 | 70581187 | 0.013 | 0.025 |

TABLE 9-continued

| | Genomic Location | | Indel Frequency | |
|---|---|---|---|---|
| | | | Mock | C. Jejuni CRISPR |
| CJ_AAVS1_24 | chr14 | 95327446 | 0.046 | 0.041 |
| CJ_AAVS1_25 | chr14 | 102331176 | 0.015 | 0.028 |
| CJ_AAVS1_26 | chr14 | 104753692 | 0.035 | 0.041 |
| CJ_AAVS1_27 | chr15 | 67686972 | 0.061 | 0.096 |
| CJ_AAVS1_28 | chr16 | 85565862 | 0.028 | 0.028 |
| CJ_AAVS1_29 | chr17 | 17270109 | 0.003 | 0 |
| CJ_AAVS1_30 | chr17 | 79782954 | 0.03 | 0.043 |
| CJ_AAVS1_31 | chr18 | 42305670 | 0.035 | 0.043 |
| CJ_AAVS1_32 | chr19 | 12826405 | 0.024 | 0.039 |
| CJ_AAVS1_33 | chr19 | 32268337 | 0.043 | 0.042 |
| CJ_AAVS1_35 | chr20 | 40758976 | 0 | 0 |
| CJ_AAVS1_36 | chr21 | 41295936 | 0.011 | 0.007 |
| CJ_AAVS1_37 | chr22 | 20990738 | 0.004 | 0.004 |
| CJ_AAVS1_38 | chr22 | 46402289 | 0.006 | 0.011 |
| CJ_AAVS1_39 | chr22 | 46426607 | 0.003 | 0 |
| CJ_AAVS1_40 | chrX | 27472673 | 0.279 | 0.318 |

Further, consensus sequences were obtained from the entire alignment of the sequences of 41 loci that showed cleavages in vitro. Consistent with previous results, PAM was actually observed as NNNNRYAC (SEQ ID NO: 1).

Example 6: Degeneracy at First Two Nucleotides of PAM

The PAM sequence of C. jejuni was found to be NNNNRYAC" as well as "NNNNACAC" in Example 5, showing degeneracy at the first two positions. In order to corroborate the degeneracy, sgRNAs were constructed respectively for the 7 PAM target sequences of C. jejuni of human AAVS1 loci, which carried G or T residues at the first two positions (TABLE 10), and analyzed for mutation efficiency in HEK293 cells.

TABLE 10

| sgRNA | Direction | PAM | Target Sequence | SEQ ID NO |
|---|---|---|---|---|
| hAAVS1-RYN1 | + | NNNNRYAC | gCCACGACCTGGTGAACACCTAGGACGCAC | 76 |
| hAAVS1-RYN2 | + | | gGCCTTATCTCACAGGTAAAACTGACGCAC | 77 |
| hAAVS1-RYN3 | + | | cTCTTGGGAAGTGTAAGGAAGCTGCAGCAC | 78 |
| hAAVS1-RYN4 | + | | aGCTGCAGCACCAGGATCAGTGAAACGCAC | 79 |
| hAAVS1-RYN5 | + | | cTGTGGGGTGGAGGGGACAGATAAAAGTAC | 80 |
| hAAVS1-RYN6 | − | | gCCGGTTAATGTGGCTCTGGTTCTGGGTAC | 81 |
| hAAVS1-RYN7 | + | | gCCATGACAGGGGCTGGAAGAGCTAGCAC | 82 |

Figure 8:
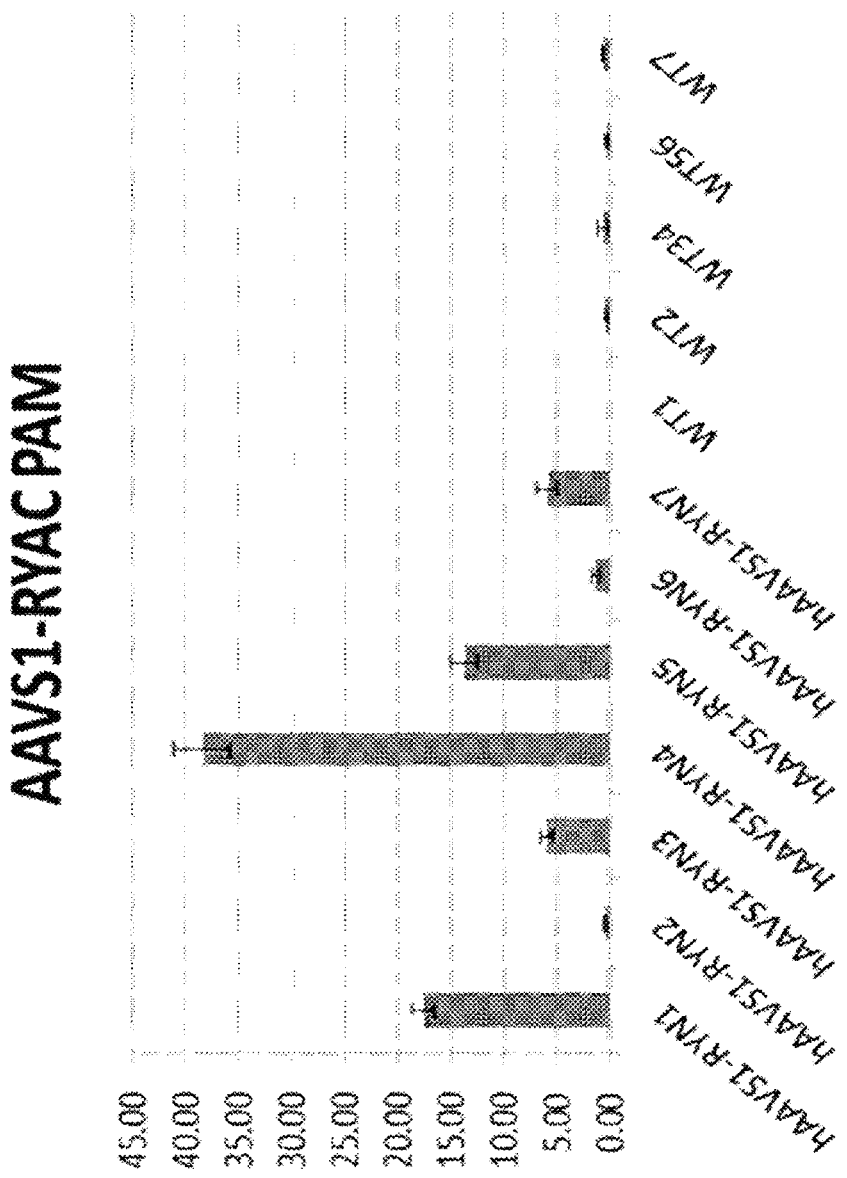
FIG. 8 shows the test results for the PAM sequences of *C. jejuni* Cas9. Seven target sites of NNNNRYAC (SEQ ID NO: 1) were analyzed for mutation efficiency. hAAVS1-RYN1-7: ratio of mutation at each site in sgRNA/Cas9-treated cells, WT1-7: ratio of mutation at each site in genomic DNA of mock-treated cells.

Of the seven constructed sgRNAs, six were found to induce mutations, demonstrating degeneracy at the first two positions of the PAM sequences (FIG. 8). Accordingly, this degeneracy increases the frequency of the PAM sequences, allowing improved accuracy of the genome editing of C. jejuni.

Example 7: Genome Editing Through C. jejuni CRISPR/CAS9 Delivery Using AAV

Representative among promising fields in which genome editing finds application are genome editing technologies for gene and cell therapy. The practical application of genome editing to therapy needs a clinically applicable vector for effectively delivering an engineered nuclease and a donor DNA to target cells in vitro or in vivo. The two most widely used engineered nuclease platforms, TALENs and RGEN, are limited to application to established gene therapy vectors due to their large sizes. In contrast, the C. jejuni RGEN of the present disclosure consists of the smallest CAS9 protein and sgRNA among the RGENs developed so far. Thanks to its small size, the C. jejuni RGEN can allow large-sized gene therapy vectors to be used in genome manipulation. For example, AAV (adeno-associated virus), serving as one of the most important vectors for gene therapy, imposes strict limitations on the size of the DNA to be carried thereby, and thus is difficult to apply to the RGEN derived from S. pyogenes, S. thermophilus, or N. meningitidis, or to the currently used engineered nuclease platform TALEN. In contrast, the C. jejuni RGEN can be applied to an AAV vector.

Figure 9:
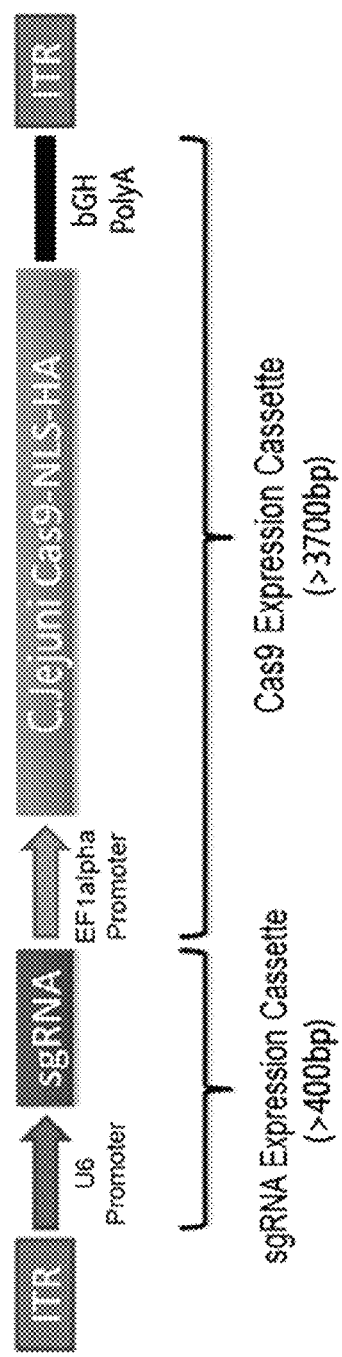
FIG. 9 is a schematic diagram showing the structure of a *C. jejuni* CRISPR/Cas9 expression AAV vector.
Figure 10:
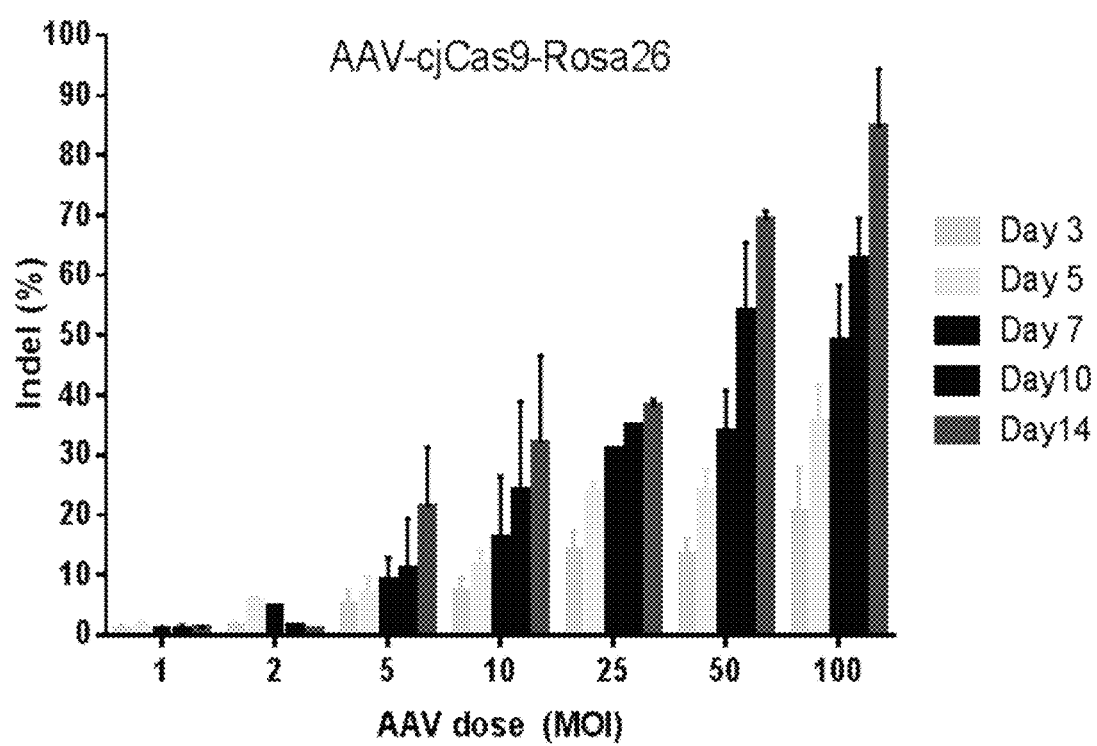
FIG. 10 shows the genome editing, performed by *C. jejuni* CRISPR/Cas9 AAV (adeno-associated virus), in the Rosa26 locus. Briefly, C2C12 cells were infected with a recombinant AAV vector carrying both Rosa26-sgRNA and *C. jejuni* Cas9 at different MOI (multiplicity of infectivity). At 3, 5, 7, 10, and 14 days post-infection, genomic DNA was isolated, and analyzed for mutation ratio by deep sequencing.

In the present disclosure, examination was made of the operation of the C. jejuni Cas9 through practical AAV delivery. To this end, an AAV vector carrying both a C. jejuni Cas9 expression cassette and an sgRNA expression cassette was constructed (FIG. 9) and used to produce AAV. After infection with the AAV, mouse C2C12 cells were quantitatively analyzed for mutations (FIG. 10). As can be seen, mutations were induced in target sites in an AAV dose- and time-dependent manner. Particularly, 4 weeks after infection at high MOI (100), mutations were induced at an efficiency of 90% or higher in the target sites.

Consequently, the C. jejuni RGEN was proven to effectively perform genome editing in cultured cells. In addition, the PAM sequence of the C. jejuni CRISPR/Cas9 system was actually determined, as the sequence proposed in previous studies was found not to be perfect. Further, the C. jejuni RGEN can be loaded into a single virus thanks to the small sizes of its elements, and thus can be used for effective genome editing.

Enrichment of Target DNA Using dCAS9:gRNA Complex

Moreover, a target DNA was isolated and enriched using the RGEN (dCas9:gRNA complex) composed of a Streptococcus pyogenes-derived, deactivated Cas9 protein and a guide RNA.

In this regard, the dCas9 protein was tagged with six consecutive His residues, so that it could be purified using Ni-NTA magnetic beads for selectively binding to the His tag. In addition, the dCas protein-sgRNA complex can be used for the selective purification of a target DNA because the complex can bind specifically to a certain DNA sequence, but lacks nuclease activity.

The RGEN (dCas9:gRNA complex) composed of a guide RNA and a deactivated Cas nuclease was tested for ability to isolate a target DNA. For this, first, the plasmid pUC19 was digested with restriction enzymes (SpaI, XmaI, XhoI) to yield plasmid DNA fragments 4134 bp, 2570 bp, and 1263 bp in length, respectively.

For each of the plasmid DNA fragments digested with the restriction enzymes, two different sgRNAs were synthesized (4134 bp_sg#1, 4134 bp_sg#2, 2570 bp_sg#1, 2570 bp_sg#2, 1263 bp_sg#1, and 1263 bp_sg#2). A purification procedure was carried out using the sgRNAs corresponding to target DNAs, singularly or in combination (4134 bp_sg#1+2, 2570 bp_sg#1+2, and 1263 bp_sg#1+2). The nucleotide sequences of the sgRNAs are listed in TABLE 11 below.

TABLE 11

| sgRNA | Target sequence | PAM Sequecne |
|---|---|---|
| 4134 bp_sg#1 | GAGAACCAGACCACCCAGAA (SEQ ID NO: 83) | GGG |
| 4134 bp_sg#2 | GGCAGCCCCGCCATCAAGAA (SEQ ID NO: 84) | GGG |
| 2570 bp_sg#1 | GTAAGATGCTTTTCTGTGAC (SEQ ID NO: 85) | TGG |
| 2570 bp_sg#2 | GATCCTTTGATCTTTTCTAC (SEQ ID NO: 86) | GGG |
| 1270 bp_sg#1 | GCCTCCAAAAAAGAAGAGAA (SEQ ID NO: 87) | AGG |
| 1270 bp_sg#2 | TGACATCAATTATTATACAT (SEQ ID NO: 88) | CGG |

\* nucleotide sequences of the sgRNAs are identical to those of the target DNA, except for U in place of T.

A total of 200 µl of a mixture solution containing DNA: dCas9 protein:sgRNA at a molar ratio of 1:20:100 was incubated at 37° C. for 1.5 hrs. Then, the solution was mixed with 50 µl of Ni-NTA magnetic beads binding specifically to His-tag, and washed twice with 200 µl of a wash buffer, followed by purifying a dCas9-sgRNA-target DNA complex with 200 µl of an eluting buffer (Bioneer, K-7200).

Thereafter, the eluate was incubated at 37° C. for 2 hrs with 0.2 mg/ml RNase A (Amresco, E866) and then at 55° C. for 45 min with 0.2 mg/ml Proteinase K to remove both the sgRNA and the dCas9 protein. The target DNA alone was precipitated in ethanol.

As a result, using the sgRNAs, whether singularly or in combinations of two thereof, for individual target DNAs, desired target DNAs could be isolated from the three DNA fragments digested by size. In addition, when multiple target DNAs were purified with combinations of sgRNA, such as a total of 4 different sgRNAs for two different target DNAs (2 sgRNAs for each target DNA), the target DNAs were associated with corresponding sgRNAs and thus purified. The results indicate that each target DNA could be isolated at a purity of 95% or higher.

Also, the purification technique is true of the Cas protein recognizing the PAM (proto-spacer-adjacent motif) sequence NNNNRYAC (SEQ ID NO: 1) of the present disclosure.

Based on the above description, it should be understood by those skilled in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to comprise all of the modifications or modified forms derived from the meaning and scope of the following claims or equivalent concepts.

What is claimed is:

1. A composition for genome editing of a target DNA sequence comprising:
   an effective amount of an isolated guide RNA comprising a first sequence forming a duplex with a complementary strand of the target DNA sequence and a second sequence interacting with a Cas protein that recognizes a proto-spacer-adjacent motif (PAM) sequence of NNNNRYAC (SEQ ID NO: 1) or a DNA encoding the isolated guide RNA, wherein the isolated guide RNA comprises a first region comprising the first sequence, and
   a second region comprising a stem-loop structure, wherein the stem-loop structure comprises a stem of 13-18 bp in length comprising a sequence of SEQ ID NO: 2 (5'-GUUUUAGUCCCUUGUG-3') and a complementary sequence thereof, and
   a recombinant Cas protein that recognizes the PAM sequence of NNNNRYAC (SEQ ID NO: 1) or a nucleic acid encoding the recombinant Cas protein for performing genome editing of the target DNA sequence in a eukaryotic cell,
   wherein the target DNA sequence is derived from a genome of the eukaryotic cell, and
   wherein the target DNA sequence is adjacent to the PAM sequence of NNNNRYAC (SEQ ID NO: 1).

2. The composition of claim 1, wherein the Cas protein is a deactivated Cas protein (dCas) or a nucleic acid that encodes the dCas.

3. The composition of claim 1, wherein the isolated guide RNA is a dual RNA comprising a crRNA (CRISPR RNA) and a tracrRNA (trans-activating crRNA).

4. The composition of claim 1, wherein the isolated guide RNA is a single-stranded guide RNA (sgRNA).

5. The composition of claim 4, wherein the sgRNA comprises a first region containing a sequence capable of forming a duplex with a complementary strand of the target DNA sequence, and a second region containing a sequence interacting with the Cas protein.

6. The composition of claim 4, wherein the sgRNA comprises a portion of a crRNA containing a sequence capable of forming a duplex with a complementary strand of the target DNA sequence, and a portion of a tracrRNA containing a sequence that interacts with the Cas protein.

7. The composition of claim 5, wherein the sequence capable of forming a duplex with a complementary strand of the target DNA sequence has a length of 17 to 23 bp.

8. The composition of claim 1, wherein the isolated guide RNA further comprises one to three additional nucleotides prior to a 5' end of the sequence capable of forming a duplex with a complementary strand of the target DNA sequence.

9. The composition of claim 8, wherein the additional nucleotides comprise guanine (G).

10. The composition of claim 1, wherein the Cas protein originates from a microorganism belonging to *Campylobacter*.

11. The composition of claim 1, wherein the Cas protein is Cas 9.

12. The composition of claim 1, wherein the isolated guide RNA comprises
   a first region comprising the first sequence, and
   a second region comprising a stem-loop structure, wherein the stem-loop structure comprises a loop of 5-10 nucleotides in length.

13. The composition of claim 12, wherein the loop comprises the sequence of SEQ ID NO: 3 (5'-AUAUUCAA-3').

* * * * *